(12) United States Patent
Nock

(10) Patent No.: US 11,241,222 B2
(45) Date of Patent: Feb. 8, 2022

(54) APPARATUS TO PERMIT SELECTIVE BIOPSY SAMPLE VISUALIZATION DURING TISSUE REMOVAL

(71) Applicant: Devicor Medical Products, Inc., Cincinnati, OH (US)

(72) Inventor: Andrew P. Nock, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 187 days.

(21) Appl. No.: 16/434,778

(22) Filed: Jun. 7, 2019

(65) Prior Publication Data

US 2019/0374210 A1 Dec. 12, 2019

Related U.S. Application Data

(60) Provisional application No. 62/682,286, filed on Jun. 8, 2018.

(51) Int. Cl.
*A61B 10/02* (2006.01)

(52) U.S. Cl.
CPC ...... *A61B 10/0275* (2013.01); *A61B 10/0283* (2013.01); *A61B 2010/0208* (2013.01); *A61B 2010/0225* (2013.01)

(58) Field of Classification Search
CPC ............ A61B 10/0275; A61B 10/0283; A61B 2010/0208; A61B 2010/0225
See application file for complete search history.

(56) References Cited

U.S. PATENT DOCUMENTS

| | | | |
|---|---|---|---|
| 5,526,822 A | 6/1996 | Burbank et al. |
| 5,928,164 A | 7/1999 | Burbank et al. |
| 6,017,316 A | 1/2000 | Ritchart et al. |
| 6,086,544 A | 7/2000 | Hibner et al. |
| 6,162,187 A | 12/2000 | Buzzard et al. |
| 6,432,065 B1 | 8/2002 | Burdorff et al. |
| 6,626,849 B2 | 9/2003 | Huitema et al. |
| 6,752,768 B2 | 6/2004 | Burdorff et al. |
| 7,442,171 B2 | 10/2008 | Stephens et al. |
| 7,648,466 B2 | 1/2010 | Stephens et al. |
| 7,837,632 B2 | 11/2010 | Stephens et al. |
| 7,854,706 B2 | 12/2010 | Hibner |
| 7,914,464 B2 | 3/2011 | Burdorff et al. |
| 7,938,786 B2 | 5/2011 | Ritchie et al. |
| 8,083,687 B2 | 12/2011 | Parihar |
| 8,118,755 B2 | 2/2012 | Hibner et al. |
| 8,206,316 B2 | 6/2012 | Hibner et al. |
| 8,241,226 B2 | 8/2012 | Hibner et al. |
| 8,454,531 B2 | 6/2013 | Speeg et al. |
| 8,622,924 B2 | 1/2014 | Speeg et al. |

(Continued)

*Primary Examiner* — Sean P Dougherty
(74) *Attorney, Agent, or Firm* — Frost Brown Todd LLC

(57) ABSTRACT

A biopsy device includes a body, a needle, a cutter, a tissue sample holder, and a sample stopping assembly. The needle extends distally from the body. The cutter is longitudinally translatable relative to the needle and defines a cutter lumen. The tissue sample holder is coupled proximally relative to the body. The cutter lumen of the cutter defines at least a portion of a fluid conduit extending between a distal end of the cutter and the tissue sample holder. The sample stopping assembly includes a rotatable strainer that is configured to selectively arrest movement of a tissue sample within the fluid conduit between the cutter and the tissue sample holder.

19 Claims, 23 Drawing Sheets

(56) References Cited

U.S. PATENT DOCUMENTS

| | | | |
|---|---|---|---|
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,095,326 B2 | 8/2015 | Ritchie et al. | |
| 9,326,755 B2 | 5/2016 | Fiebig et al. | |
| 9,345,457 B2 | 5/2016 | Speeg et al. | |
| 9,486,186 B2 | 11/2016 | Fiebig et al. | |
| 9,724,076 B2 | 8/2017 | Fiebig et al. | |
| 10,729,856 B1 * | 8/2020 | Nock | A61B 10/0096 |
| 10,905,404 B2 * | 2/2021 | Choung | A61B 10/0283 |
| 2006/0074345 A1 | 4/2006 | Hibner | |
| 2009/0131821 A1 | 5/2009 | Speeg et al. | |
| 2010/0152610 A1 | 6/2010 | Parihar et al. | |
| 2010/0160819 A1 | 6/2010 | Parihar et al. | |
| 2012/0109007 A1 * | 5/2012 | Rhad | A61B 10/0096 600/567 |
| 2013/0324882 A1 | 12/2013 | Mescher | |
| 2014/0039343 A1 * | 2/2014 | Mescher | A61B 10/0275 600/563 |
| 2017/0311935 A1 * | 11/2017 | Choung | A61B 10/0096 |
| 2018/0153524 A1 | 6/2018 | Nock et al. | |
| 2018/0153529 A1 | 6/2018 | Nock et al. | |
| 2018/0242959 A1 | 8/2018 | Keller | |
| 2019/0059865 A1 * | 2/2019 | Oyola | A61B 10/0096 |

* cited by examiner

APPARATUS TO PERMIT SELECTIVE BIOPSY SAMPLE VISUALIZATION DURING TISSUE REMOVAL

PRIORITY

This application claims priority to U.S. Provisional Patent App. No. 62/682,286 entitled "Apparatus to Permit Selective Biopsy Sample Visualization During Tissue Removal," filed on Jun. 8, 2018, the disclosure of which is incorporated by reference herein.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological).

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 21, 2012; U.S. Pat. No. 8,206,316, entitled "Tetherless Biopsy Device with Reusable Portion," issued Jun. 26, 2012; U.S. Pat. No. 8,241,226, entitled "Biopsy Device with Rotatable Tissue Sample Holder," issued Aug. 14, 2012; U.S. Pat. No. 8,764,680, entitled "Handheld Biopsy Device with Needle Firing," issued Jul. 1, 2014; U.S. Pat. No. 8,801,742, entitled "Needle Assembly and Blade Assembly for Biopsy Device," issued Aug. 12, 2014; U.S. Pat. No. 8,938,285, entitled "Access Chamber and Markers for Biopsy Device," issued Jan. 20, 2015; U.S. Pat. No. 8,858,465, entitled "Biopsy Device with Motorized Needle Firing," issued Oct. 14, 2014; U.S. Pat. No. 9,326,755, entitled "Biopsy Device Tissue Sample Holder with Bulk Chamber and Pathology Chamber," issued May 3, 2016; and U.S. Pat. No. 9,345,457, entitled "Presentation of Biopsy Sample by Biopsy Device," issued May 24, 2016. The disclosure of each of the above-cited U.S. patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006, now abandoned; U.S. Pat. Pub. No. 2009/0131821, entitled "Graphical User Interface For Biopsy System Control Module," published May 21, 2009, now abandoned; U.S. Pat. Pub. No. 2010/0160819, entitled "Biopsy Device with Central Thumbwheel," published Jun. 24, 2010; and U.S. Pat. Pub. No. 2013/0324882, entitled "Control for Biopsy Device," published Dec. 5, 2013, now abandoned. The disclosure of each of the above-cited U.S. patent application Publications, U.S. Non-Provisional patent applications, and U.S. Provisional patent applications is incorporated by reference herein.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
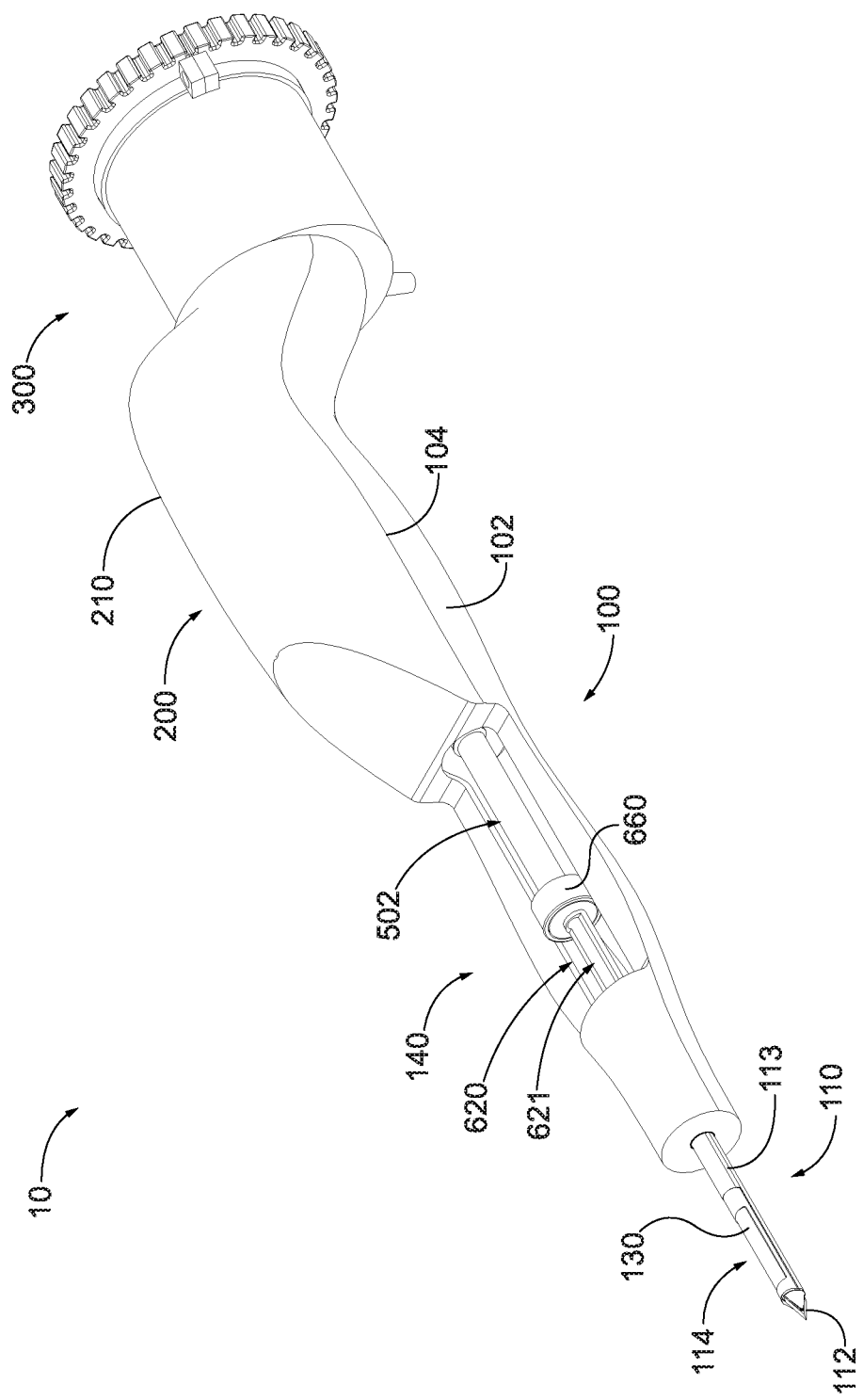
FIG. 1 depicts perspective view of an exemplary biopsy device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. EXEMPLARY BIOPSY DEVICE

FIG. 1 shows an exemplary a biopsy device (10) that may be used in a breast biopsy system including, in some examples, a vacuum control module (not shown). Biopsy device (10) of the present example comprises a probe (100) and a holster (200). A needle (110) extends distally from probe (100) and is inserted into a patient's tissue to obtain tissue samples. These tissue samples are deposited in a tissue sample holder (300) at the proximal end of probe (100), as will also be described in greater detail below.

Holster (200) of the present example is selectively attachable to probe (100) to provide actuation of various components within probe (100). In the present configuration, holster (200) is a reusable component, while probe (100) and tissue sample holder (300) are disposable. It should be understood that the use of the term "holster" herein should not be read as requiring any portion of probe (100) to be inserted into any portion of holster (200). For instance, in the present example, holster (200) includes a set of prongs (not shown) or other retention features that are received by probe (100) to releasably secure probe (100) to holster (200). Probe (100) also includes a set of resilient tabs (not shown) or other suitable release features that may be pressed inwardly to disengage the prongs, such that a user may simultaneously depress both of the tabs then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition, or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a Hall Effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured for handheld use and be used under ultrasonic guidance. Of course, biopsy device (10) may instead be used under stereotactic guidance, MRI guidance, PEM guidance, BSGI guidance, or otherwise. It should also be understood that biopsy device (10) may be sized and configured such that biopsy device (10) may be operated by a single hand of an operator. In particular, an operator may grasp biopsy device (10), insert needle (110) into a patient's breast, and collect one or a plurality of tissue samples from within the patient's breast, all with just using a single hand. Alternatively, an operator may grasp biopsy device (10) with more than one hand and/or with any desired assistance. In still other examples, biopsy device (10) can be configured to be secured to a table or other fixture without handheld operation.

In some settings, whether biopsy device (10) is handheld or mounted to a fixture, the operator may capture a plurality of tissue samples with just a single insertion of needle (110) into the patient's breast. Such tissue samples may be deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

Holster (200) of the present example includes an outer housing (210) that is configured to at least partially encompass the internal components of holster (200). Although not shown, it should be understood that holster (200) of the present example includes one or more motors and/or other actuators that are configured to drive various components of probe. To communicate power or movement to probe (100), holster (200) can include one or more gears. For instance, in some examples, one or more gears at least partially extend through an opening in outer housing (210). The opening in outer housing (210) can be configured to align with a corresponding opening associated with probe (100) to thereby permit the one or more gears of holster (200) to mesh with one or more corresponding gears of probe (100).

Although not shown, it should be understood that holster (200) may also include various cables that are configured to couple holster (200) to a control module or another control feature. Suitable cables may include electrical cables, rotary drive cables, pneumatic cables, or some combination thereof. Accordingly, it should be understood that in some examples, internal components within holster (200) may be powered by electrical power (electrical cables), rotary power (rotary drive cable), and/or pneumatic power (pneumatic cables). Alternatively, in some examples the cables are omitted entirely and holster (200) can be battery powered with motors and vacuum pumps being entirely contained within holster (200).

As described above, holster (200) of the present example is configured as a reusable portion, while probe (100) is configured as a disposable portion. In some contexts, it may be desirable to maintain sterility of reusable components during a biopsy procedure. Accordingly, in some instances it may be desirable to use holster (200) in connection with certain features to maintain the sterility of holster (200), while also maintaining functionality of holster (200). Merely exemplary features and methods for maintaining the sterility of holster (200) are shown and described in U.S. patent Ser. No. 15/829,464, entitled "Functional Cover for Biopsy Device," filed on Dec. 1, 2017, the disclosure of which is incorporated by reference herein.

Probe (100) of the present example includes a needle (110) extending distally from probe (100) that is inserted into a patient's tissue to obtain tissue samples. These tissue samples are deposited in a tissue sample holder (300) at the proximal end of probe (100). In some examples, a vacuum control module (not shown) is coupled with probe (100) via a valve assembly (not shown) and tubes (not shown), which is operable to selectively provide vacuum, saline, atmospheric air, and venting to probe (100). By way of example only, the internal components of the valve assembly of the present example may be configured and arranged as described in U.S. Pat. No. 9,724,076, entitled "Biopsy Device Valve Assembly," issued Aug. 8, 2017, the disclosure of which is incorporated by reference herein.

As described above with respect to holster (200), probe (100) is selectively couplable to holster (200) so that holster (200) may provide power or otherwise actuate probe (100). In particular, probe (100) includes an outer housing (102) that includes a holster receiving portion (104) that is configured to receive holster (200). In some examples, holster receiving portion (104) includes an opening that is configured to align with a corresponding opening of holster (200). One or more drive gears (not shown) are exposed through the opening in outer housing (102) and are operable to drive a cutter actuation mechanism in probe (100). The one or more drive gears of probe (100) mesh with the one or more gears of holster (200) when probe (100) and holster (200) are coupled together. Accordingly, holster (200) may provide mechanical power or otherwise drive movement of components within probe (100) via gears of probe (100) and holster (200).

Outer housing (102) of probe (100) additionally defines a sample inspection area (140) disposed distally on the exterior of outer housing (102) adjacent to the distal end of outer housing (102). In some examples, it may be desirable for an operator to view samples as they are collected by needle (110). For instance, and as will be described in greater detail below, in the present example tissue sample holder (300) is configured to collect tissue sample in a bulk configuration. While this configuration of tissue sample collection may enhance tissue sample capacity, the ability to visualize individual tissue samples may be reduced due to multiple tissue samples being comingled within a common space. Accordingly, sample inspection area (140) is configured to permit an operator to visualize individual tissue samples as they are collected via needle (110). As will be described in greater detail below, sample inspection area (140) permits an operator to visually inspect a severed tissue sample prior to transportation of the severed tissue sample to tissue sample holder (300). It should be understood that in some examples, various components associated with sample inspection area (140) can be configured to selectively open or close to also permit individual samples to be accessed, manipulated, and physically inspected prior to transport to tissue sample holder (300). Examples of such components will be described in greater detail below.

Needle (110) of the present example comprises a cannula (113) having a piercing tip (112), and a lateral aperture (114) located proximal to tip (112). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," filed Jun. 1, 2011, the disclosure of which is incorporated by reference herein. As another merely illustrative example, tip (112) may be configured in accordance with at least some of the teachings in U.S. Pat. No. 9,486,186, entitled "Biopsy Device with Slide-In Probe," issued on Nov. 8, 2016, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (130) having a sharp distal edge (132) is located within needle (110). Cutter (130) is operable to rotate and translate relative to needle (110) and past lateral aperture (114) to sever a tissue sample from tissue protruding through lateral aperture (114). For instance, cutter (130) may be moved from an extended position to a retracted position, thereby "opening" lateral aperture (114) to allow tissue to protrude therethrough; then from the retracted position back to the extended position to sever the protruding tissue. Severed tissue samples can then be transported proximally though needle (110) via a lumen defined by cutter (130).

In some examples it may be desirable to rotate needle (110) to orient lateral aperture (114) at a plurality of desired angular positions about the longitudinal axis of needle (110). In the present example, needle (110) can be rotated by a motor disposed in probe (100) or holster (200). In other examples, needle (110) is manually rotatable by a thumbwheel on probe (100) or needle hub directly overmolded onto needle (110). Regardless, it should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pat. No. 9,345,457, issued May 24, 2016, the disclosure of which is incorporated by reference herein, and/or in accordance with the teachings of any other reference cited herein.

Tissue sample holder (300) is selectively coupleable to the proximal end of probe (100). In the present example, tissue sample holder (300) is configured to receive a plurality of tissue samples in a variety of tissues sample collection configurations. By way of example only, suitable tissue collection configurations may include bulk tissue sample collection configurations and/or individual sample collection configurations. In a bulk sample collection configuration, acquired tissue samples are comingled within one or more tissue sample collection chambers. By contrast, in an individual sample collection configuration, tissue samples are segregated in individual sample compartments. While tissue sample holder (300) in some examples may be configured for exclusively bulk sample collection or individual sample collection, it should be understood that in other examples both tissue sample collection configurations can be combined in a single tissue sample holder (300). Merely exemplary configurations for tissue sample holder shown and described in U.S. Pat. Pub. No. 2018/0242959, entitled "Tissue Sample Holder with Bulk Tissue Collection Feature," published Aug. 30, 2018; and U.S. Pat. Pub. No. 2018/0153524, entitled "Multi-Chamber Tissue Sample Cup for Biopsy Device," published Jun. 7, 2018, the disclosures of which are incorporated by reference herein.

II. EXEMPLARY TISSUE ACQUISITION ASSEMBLY

Figure 2:
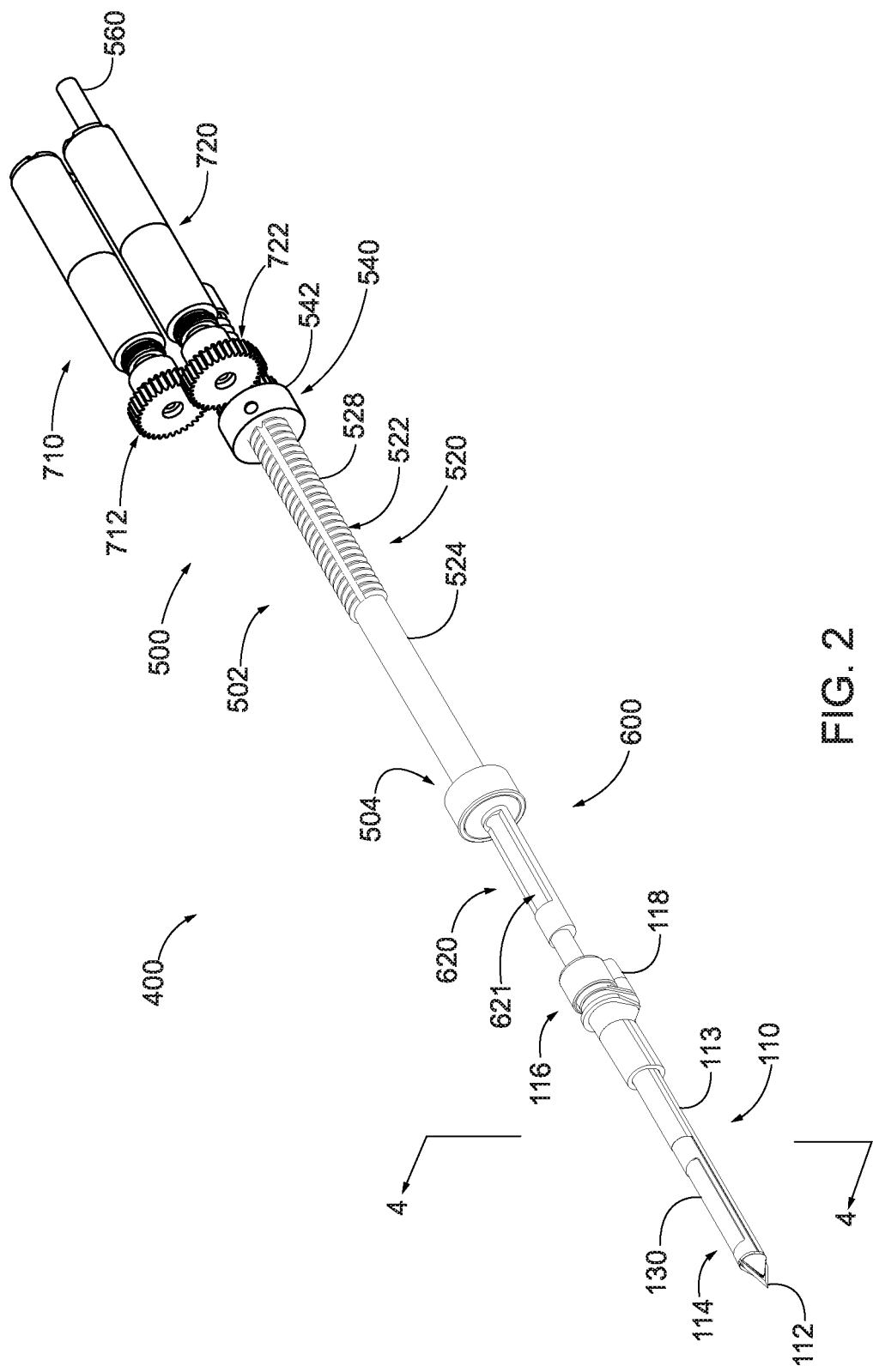
FIG. 2 depicts a perspective of a tissue sample acquisition assembly of the biopsy device of FIG. 1.

As best seen in FIG. 2, probe (100) further includes a tissue acquisition assembly (400). As can be seen, tissue acquisition assembly (400) comprises needle (110), cutter (130), a cutter actuation assembly (500), and a gate assembly (600). As described above, needle (110) comprises a cannula (113) and a tissue piercing tip (112). Cannula (113) of the present example comprises a generally circular cross-sectional shape, defining a lumen therein such that cannula (113) is configured to receive cutter (130) coaxially within the lumen of cannula (113). Tissue piercing tip (112) is secured to the distal end of cannula (113). In the present example, tissue piercing tip (112) is a solid homogeneous piece of material that is ground to form a plurality of facets that together define the sharp point of tissue piercing tip (112). Although tissue piercing tip (112) of the present example is shown as a single part, it should be understood that in other examples tissue piercing tip (112) comprises a multiple part assembly. Merely exemplary alternative configurations for tissue piercing tip (112) are shown and described in U.S. Pat. No. 8,801,742, entitled "Needle Assembly and Blade Assembly for Biopsy Device," issued on Aug. 12, 2014, the disclosure of which is incorporated by reference herein.

Figure 3:
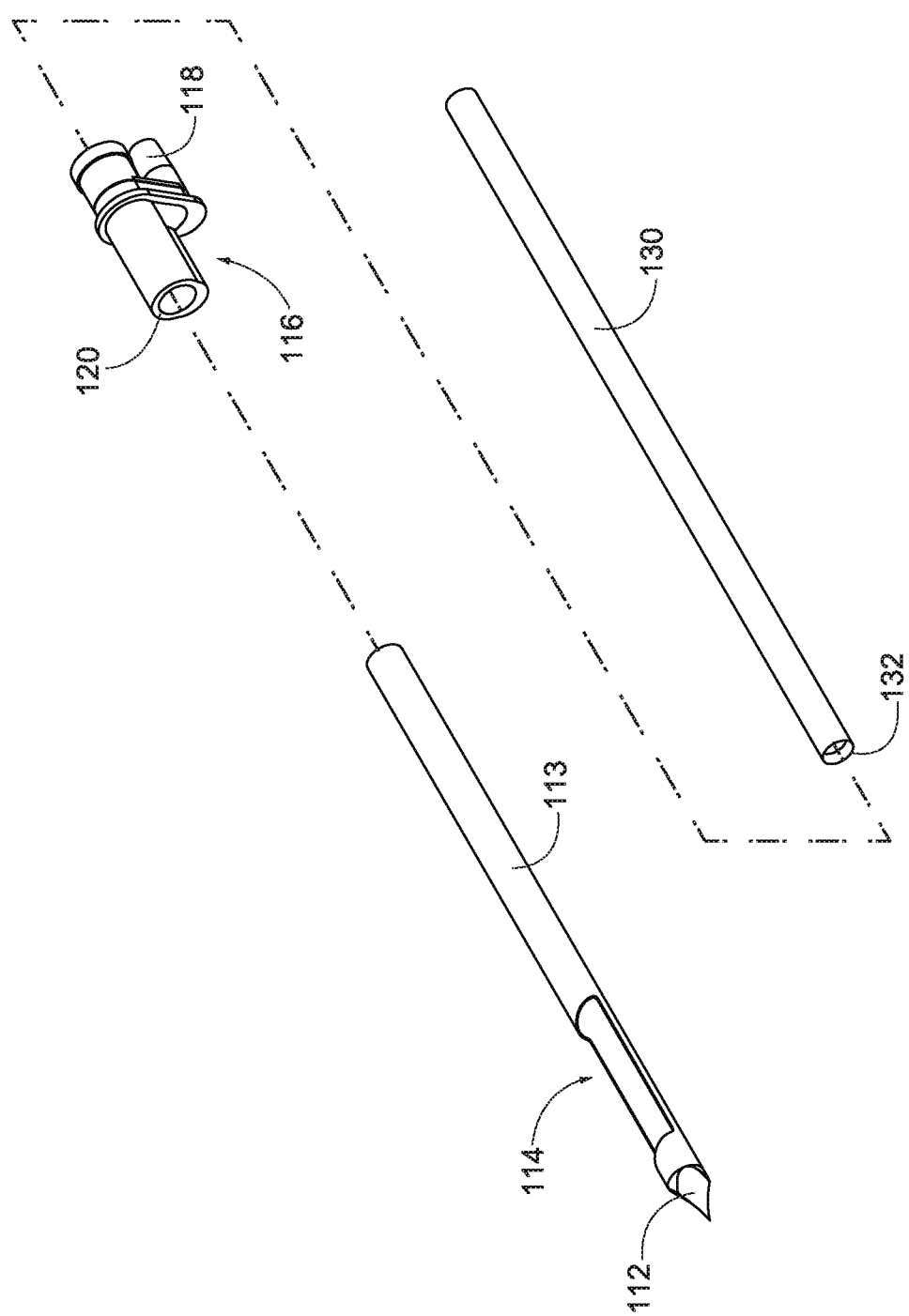
FIG. 3 depicts an exploded perspective view of a needle of the tissue acquisition assembly of FIG. 2.
Figure 4:
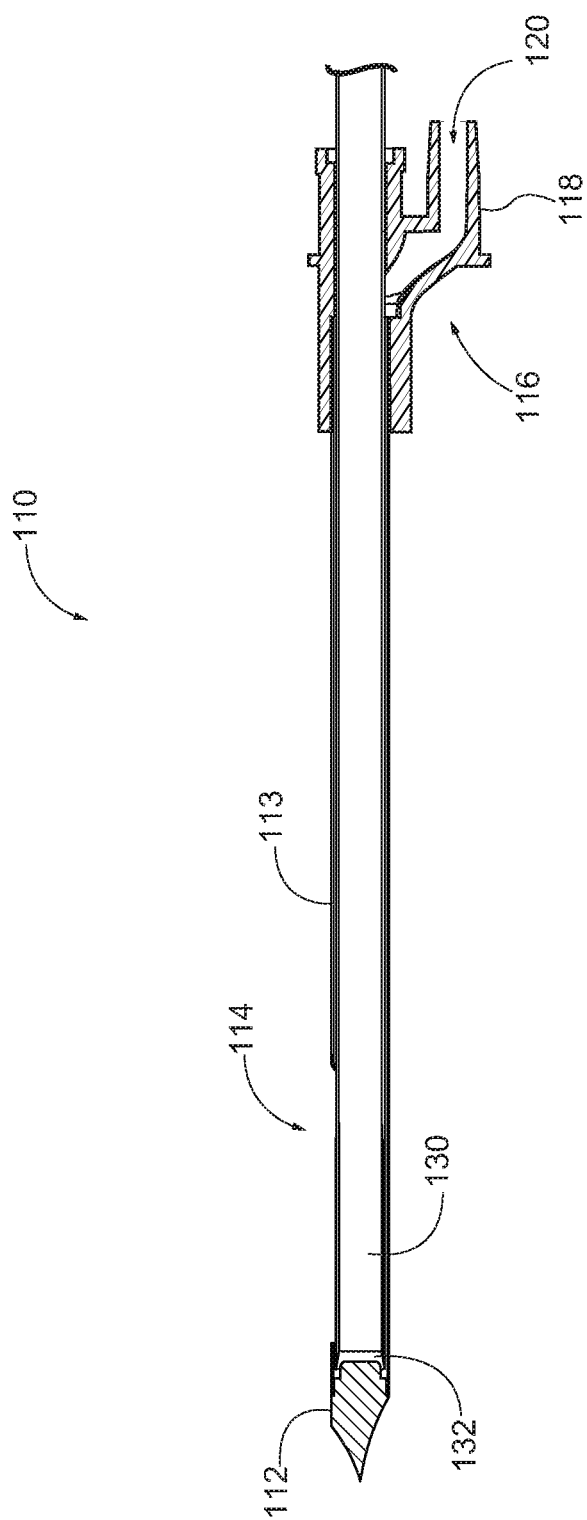
FIG. 4 depicts a side cross-sectional view of the needle of FIG. 3, with the cross-section taken along line 4-4 of FIG. 2.
Figure 5:
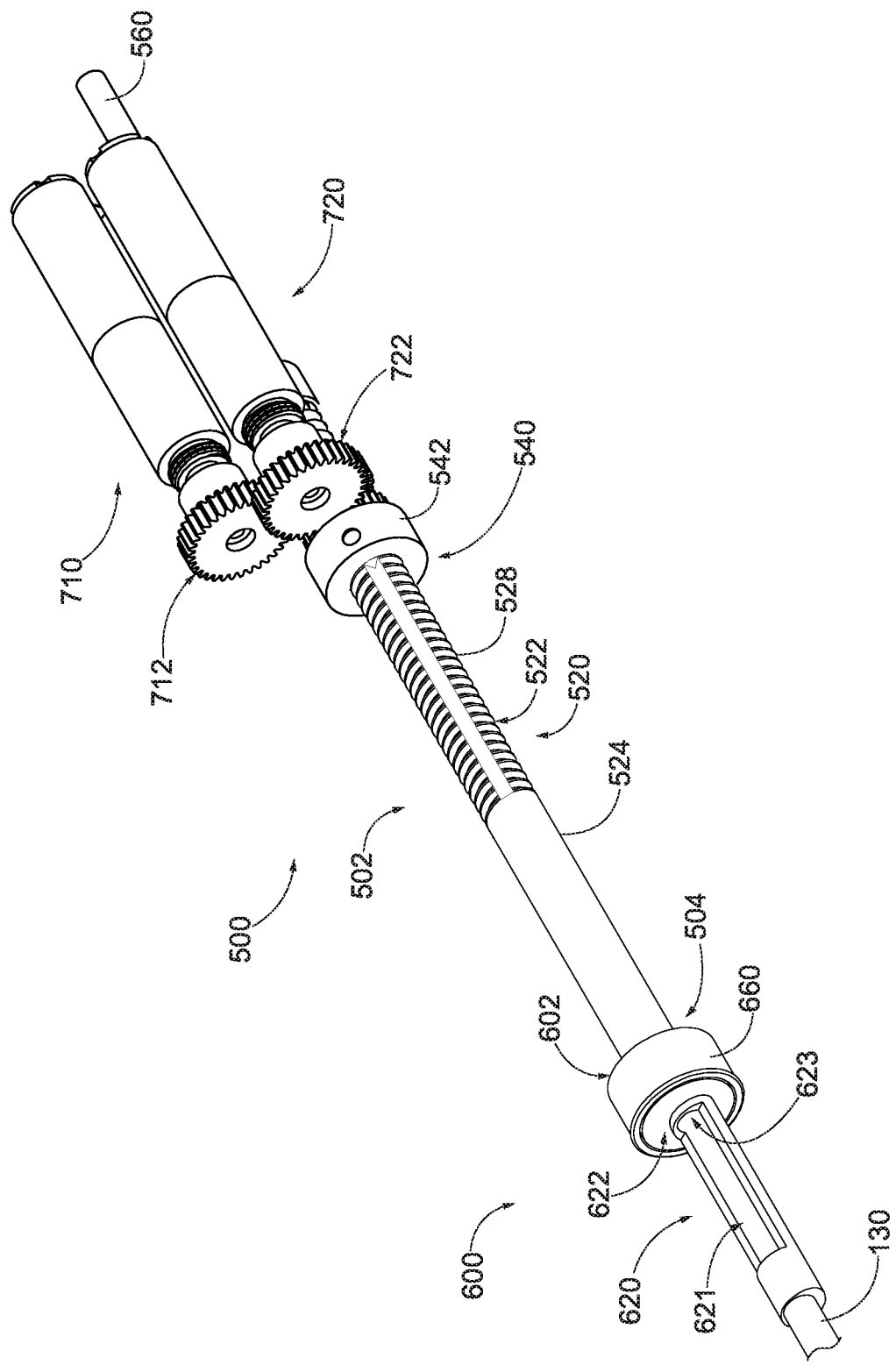
FIG. 5 depicts a perspective view of a gate assembly and cutter actuation assembly of the sample acquisition assembly of FIG. 2.

As can be best seen in FIGS. 3 and 4, needle (110) additionally includes a manifold (116) secured to the distal end of cannula (113). Manifold (116) is generally configured to direct fluid into the lumen of cannula (113). Manifold (116) includes a port (118) and a lumen (120) communicating with port (118). Although not shown, it should be understood that a tube or valve assembly can be connected to port (118) to communicate fluids into lumen (120). Lumen (120) extends through manifold (116) and into communication with the lumen of cutter (130). Accordingly, it should be understood that fluids may be directed to port (118) and into lumen (120) to communicate fluids to the lumen of cannula (113). In use, any suitable fluid may be communicated through manifold (116). For instance, in some examples manifold (116) is used to provide atmospheric air to the lumen of cannula (113). In such examples, atmospheric air may be desirable to enhance transportation of tissue samples through cutter (130) by providing a pressure differential on either side of the tissue sample. In addition, in some examples manifold (116) is used to provide vacuum and/or saline to assist with a biopsy procedure.

Cutter actuation assembly (500) is shown in FIGS. 5-8. As can be seen, cutter actuation assembly comprises a cutter drive member (502), a translation member or gear (530), a rotation member or gear (540) and a transfer tube (560). Cutter drive member (502) comprises a gate portion (504) and a drive portion (520). As will be described in greater detail below, at least a portion of gate portion (504) is generally configured to couple to at least a portion of gate assembly (600) to communicate rotational and translational motion of cutter drive member (502) to gate assembly (600). As will also be described in greater detail below, at least a portion of gate assembly (600) is coupled to cutter (130) to communicate rotational and translational motion of gate assembly (600) to cutter (130). Thus, it should be understood that rotation and translation of cutter drive member (502) results in corresponding rotation and translation of cutter (130) via the coupling between at least a portion of gate portion (504) and at least a portion of gate assembly (600).

Figure 6:
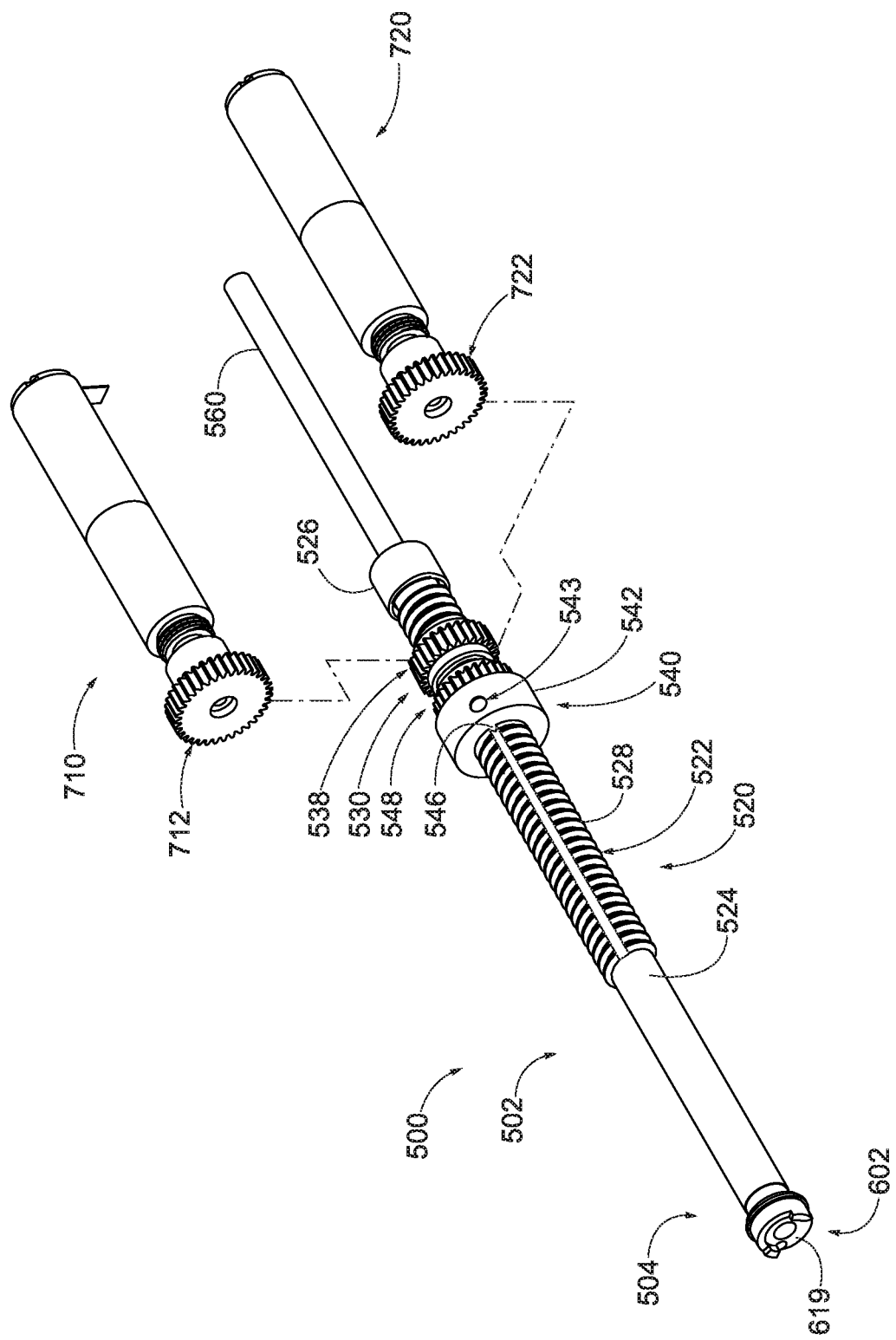
FIG. 6 depicts a partially exploded view of the cutter actuation assembly of FIG. 5.

As seen in FIG. 6, cutter drive assembly (500) of the present example is actuated by two independent drivers or motors (710, 720). Each motor (710, 720) corresponds to translation member (530) and rotation member (540), respectively. Thus, motors (710, 720) include a translation motor (710) corresponding to translation member (530) and a rotation motor (720) corresponding to rotation member (540). Although not shown, in some examples motors (710, 720) can be incorporated into holster (200) with at least a portion of motors (710, 720) or assemblies associated therewith protruding from holster (200) to engage translation member (530) and rotation member (540), which can be disposed within probe (100). It should be understood that cutter drive assembly (500) is configured for independent actuation of translation member (530) and rotation member (540). As will be described in greater detail below, this configuration permits cutter (130) to be moved so that translational movement is independent of rotational movement.

Drive portion (520) of cutter drive member (502) comprises a threaded portion (522) and a longitudinal channel (528) extending axially along cutter drive member (502) through threaded portion (522). Threaded portion (522) is disposed between a distal no-pitch zone (524) and a proximal no-pitch zone (526). As will be described in greater detail below, threaded portion (522) is generally configured to engage with translation member (530) to provide translation of cutter drive member (502). Similarly, longitudinal channel (528) is configured to engage rotation member (540) to provide rotation of cutter drive member (502). As will also be described in greater detail below, each no-pitch zone (524, 526), is configured to permit rotation of cutter drive member (502) without translation of cutter drive member (502).

Figure 7:
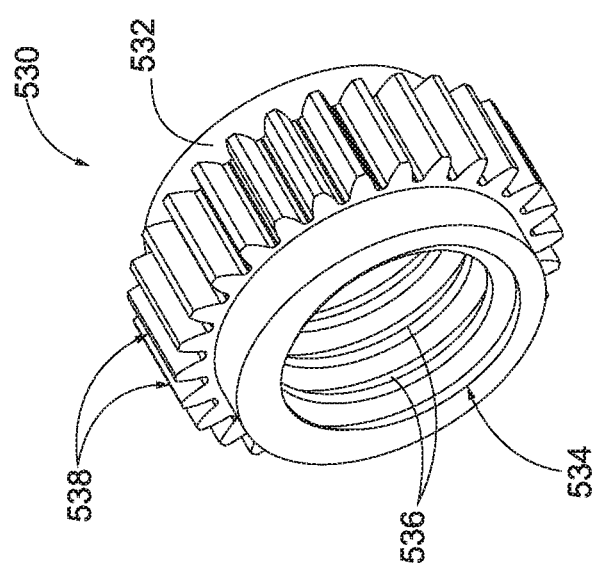
FIG. 7 depicts a perspective view of a translation member of the cutter actuation assembly of FIG. 5.
Figure 9:
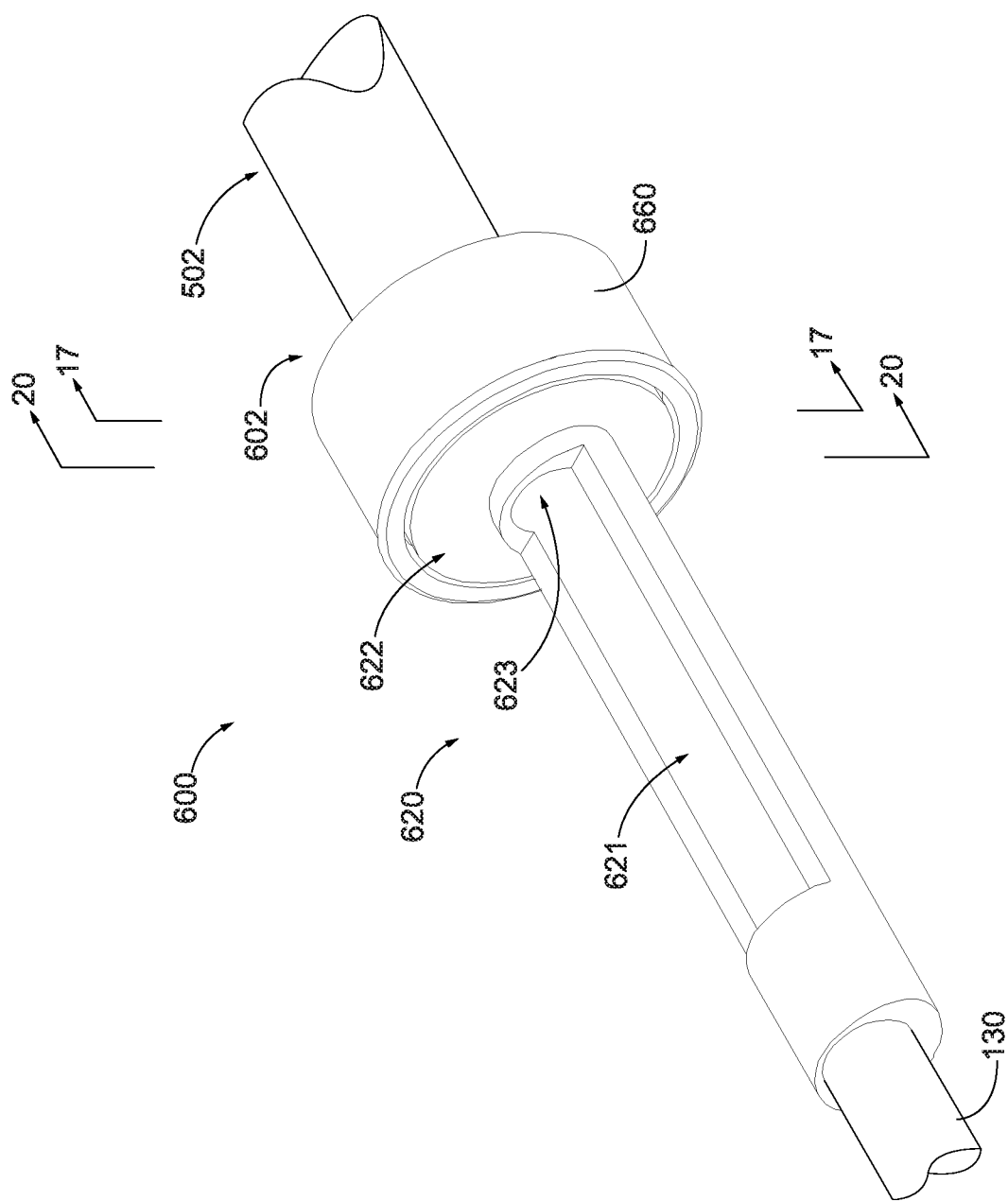
FIG. 9 depicts a detailed perspective view of the gate assembly of FIG. 5.

As best seen in FIG. 7, translation member or gear (530) comprises a cylindrical body (532). Cylindrical body (532) is generally hollow, defining a bore (534) extending axially therethrough. The interior of bore (534) includes a plurality of threads (536) that are configured to engage threaded portion (522) of cutter drive member (502). As will be described in greater detail below, engagement between threads (536) of translation member (530) and threaded portion (522) of cutter drive member (502) is generally configured to cause translation of cutter drive member (502) in response to rotation of cutter drive member (502).

Translation member (530) further comprises a plurality of teeth (538) extending outwardly from the exterior of cylindrical body (532). Teeth (538) are configured to engage corresponding teeth (712) of motor (710). Although not shown, it should be understood that at least a portion of translation member (530) extends through an opening in outer housing (102) of probe (100) to permit engagement between translation member (530) and teeth (712) of motor (710). As will be described in greater detail below, rotation of translation member (530) via motor (710) is generally configured to cause translation of cutter drive member (502) to thereby translate cutter (130).

Figure 8:
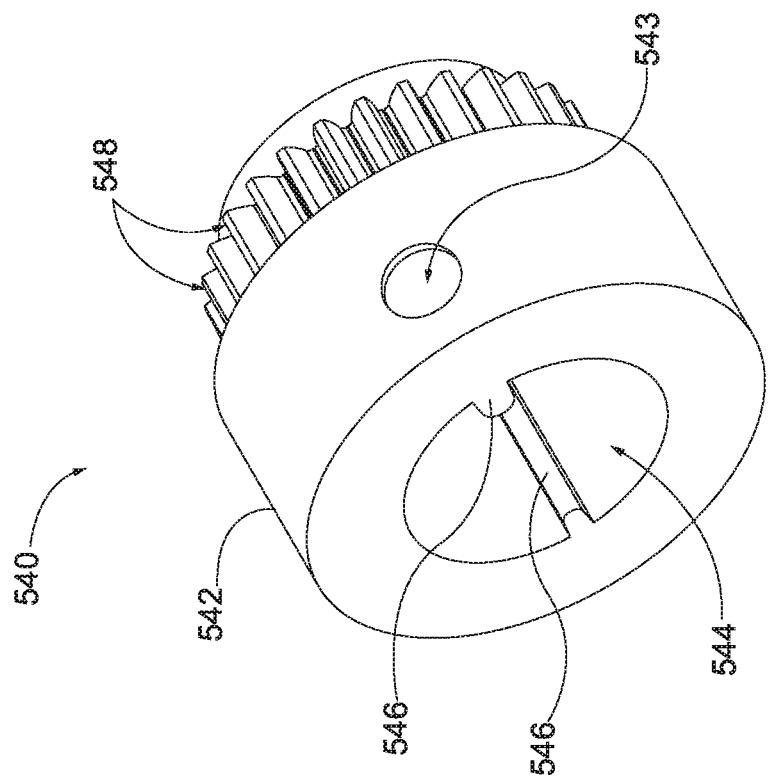
FIG. 8 depicts a perspective view of a rotation member of the cutter actuation assembly of FIG. 5.

As seen in FIG. 8, rotation member (540) comprises a cylindrical body (542) that is configured to fit around the outer diameter of cutter drive member (502). Cylindrical body (542) of rotation member (540) is generally hollow, defining a bore (544) extending axially there through. The interior of bore (544) includes a pair of keys (546) extending radially inwardly toward the center of bore (544). As will be described in greater detail below, each key (546) is configured to engage longitudinal channel (528) of cutter drive member (502). Although not shown, it should be understood that cutter drive member (502) includes another substantially identical longitudinal channel (528) on the opposite side of cutter drive member (502) such that both keys (546) are received within a corresponding longitudinal channel (528). As will be understood, this configuration permits rotation member (540) to rotate cutter drive member (502) in response to rotation of rotation member (540).

The exterior of cylindrical body (542) defines a lateral bore (543). Lateral bore (543) is generally configured to function in connection with a sensor or other device to sense the rotational position of cutter (130) by way of rotation member (540). For instance, in some examples lateral bore (543) can receive a magnet or other identifier. In such examples, a magnetic sensor can be placed adjacent to rotation member (540) to detect when the magnet is disposed adjacent to the sensor. Such a configuration may be desirable in configurations where at least one rotational position of cutter (130) is desired.

Rotation member (540) further comprises a plurality of teeth (548) extending outwardly from the exterior of cylindrical body (542). Teeth (548) are configured to engage corresponding teeth (722) of motor (720). Although not shown, it should be understood that at least a portion of rotation member (540) extends through an opening in outer housing (102) of probe (100) to permit engagement between rotation member (540) and teeth (722) of motor (720). As will be described in greater detail below, rotation of rotation member (540) via motor (720) is generally configured to cause rotation of cutter drive member (502) to thereby rotate cutter (130).

Although specific examples of cutter drive assembly (500) are shown and described herein, it should be understood that various alternative configurations can be used. For instance, as described above, cutter drive assembly (500) of the present example is generally configured to move cutter (130) with independent rotation and translation. However, in other examples, cutter drive assembly (500) can be configured to move cutter (130) with a fixed relationship between translation and rotation. In some examples, various components of cutter drive assembly (500) can be configured in accordance with the teachings of US Pub. No. 2018/0153529, entitled "Apparatus to Allow Biopsy Sample Visualization During Tissue Removal," published on Jun. 7, 2018.

Transfer tube (560) extends from cutter drive member (502) to tissue sample holder (300) to provide communication of tissue samples from cutter drive member (502) to tissue sample holder (300). A lumen (not shown) is defined within transfer tube (560). A corresponding lumen (503) is extends through cutter drive member (502). Accordingly, it should be understood that the lumen of transfer tube (560) and lumen (503) of cutter drive member (502) together define a continuous path for tissue samples to flow through cutter drive member (502) and transfer tube (560) to tissue sample holder (300). As will be described in greater detail below, tissue samples generally flow through cutter (130) into gate assembly (600) and then pass through cutter drive member (502) and transfer tube (560) before finally being deposited within tissue sample holder (300). Thus, it should be understood that both lumen (562) of transfer tube (560) and lumen (503) of cutter drive member (502) are in fluid communication with the interior of cutter (130).

Gate assembly (600) is shown in greater detail in FIGS. 9-17. As will be described in greater detail below, gate assembly (600) is generally configured to temporarily cease progression of a severed tissue sample for inspection through sample inspection area (140) of probe (100) as the severed tissue sample progresses through cutter (130) and transfer tube (560) to tissue sample holder (300). It should be understood that inspection through sample inspection area (140) can include visual inspection, inspection through tissue analysis sensors, and/or physical inspection by removal of the tissue sample through sample inspection area (140).

Figure 10:
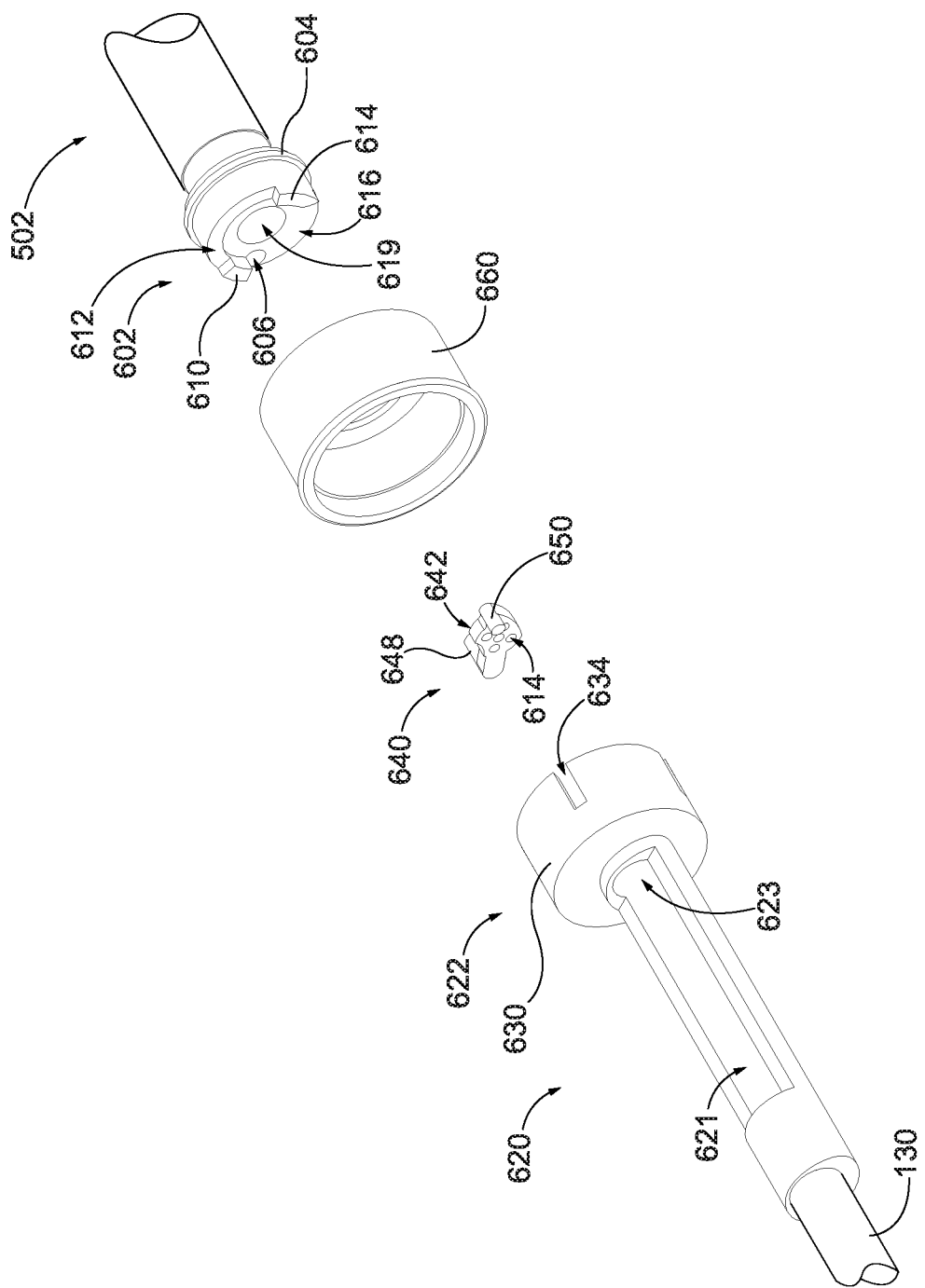
FIG. 10 depicts an exploded perspective view of the gate assembly of FIG. 5.
Figure 11:
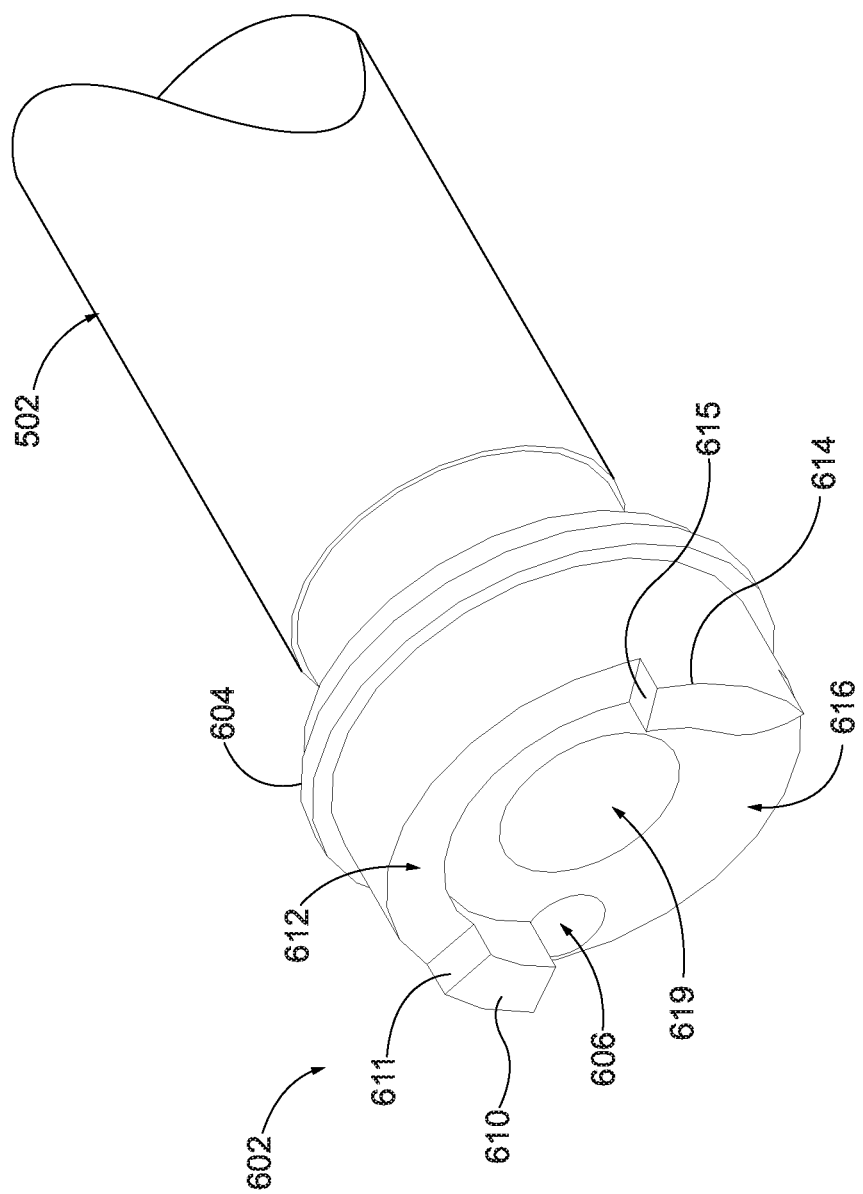
FIG. 11 depicts a detailed perspective view of a proximal coupler of the gate assembly of FIG. 5.
Figure 12:
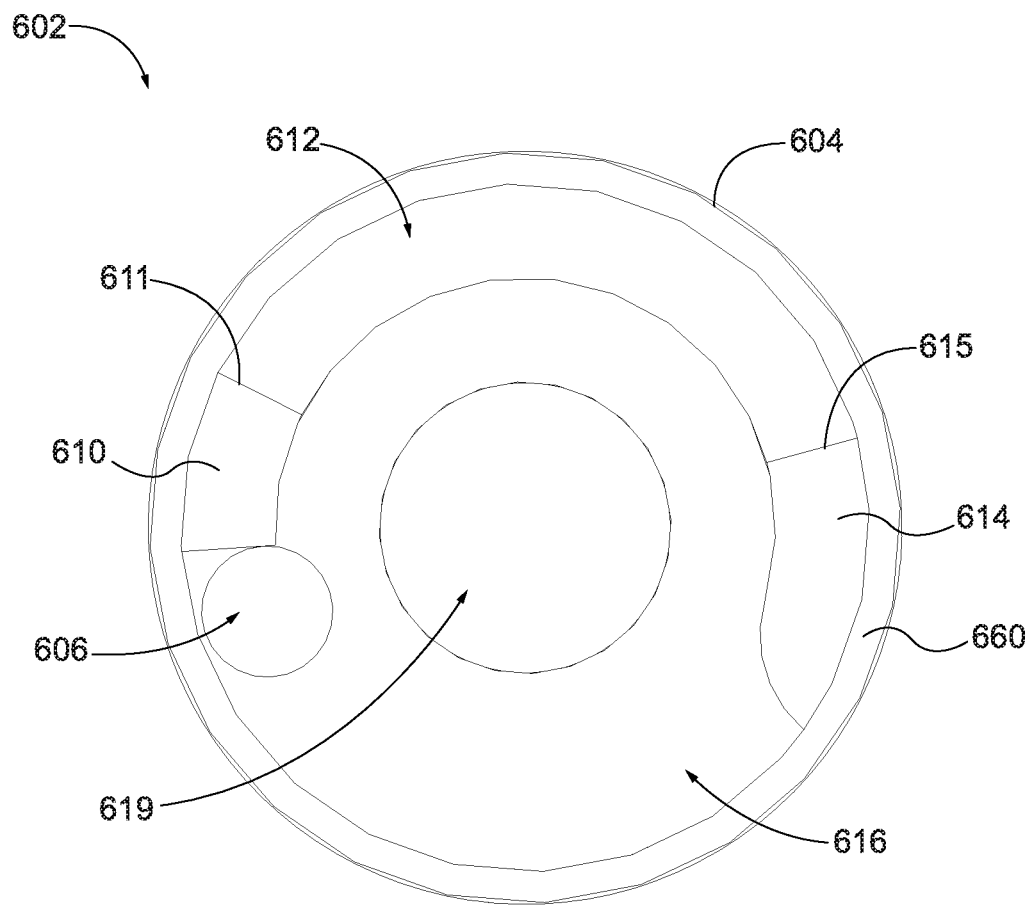
FIG. 12 depicts a front elevational view of the proximal coupler of FIG. 11.

As best seen in FIG. 10, gate assembly (600) comprises a proximal coupler (602), an inspection member (620) including a distal coupler (622), a filter gate (640) (also referred to as a strainer) disposed between proximal coupler (602) and distal coupler (622), and a coupling collar (660). As best seen in FIG. 11, proximal coupler (602) is disposed on the distal end of cutter drive member (502). Although proximal coupler (602) is shown as being integral with cutter drive member (502) in the present example, it should be understood that in some examples, proximal coupler (602) can be a discrete component attached to cutter drive member (502).

Regardless, it should be understood that proximal coupler (602) is generally configured to at least partially drive movement of filter gate (640) while also transferring movement of cutter drive member (502) to cutter (130) by way of inspection member (620).

Proximal coupler (602) of the present example comprises a proximal flange (604), a pivot opening (606), a first actuator (610), and a second actuator (614), and a transport lumen (619) extending through proximal coupler (602). Proximal flange (604) is disposed coaxially around the exterior body portion of proximal coupler (602). As will be described in greater detail below, proximal flange (604) is generally configured to engage with coupling collar (660) to seal the interior of proximal coupler (602) relative to the exterior of proximal coupler (602).

Pivot opening (606) extends proximally from a distal face of proximal coupler (602). As will be described in greater detail below, pivot opening (606) is generally configured to receive a mating portion of filter gate (640). This configuration generally permits filter gate (640) to pivot relative to the axial center of pivot opening (602). To support this pivoting functionality, pivot opening (606) is generally cylindrical in shape. In addition, to support pivoting of filter gate (640) through a specific predetermined path relative to transport lumen (619), the axial center of pivot opening (602) is generally offset relative to the axial center of proximal coupler (602) and/or transport lumen (619). Thus, pivot opening (602) generally acts as an axial ground to permit filter gate (640) to pivot between a sample stopping position that blocks pivot opening (606) and a transport position that opens pivot opening (606).

First actuator (610) and second actuator (614) extend outwardly from the distal face the body of proximal coupler (602). First actuator (610) and second actuator (614) are generally positioned on opposite sides of the outer diameter of proximal coupler (602). This positioning defines a drive slot (612) and a pivot slot (616) between first actuator (610) and second actuator (614). As will be described in greater detail below, a drive face (611) of first actuator (610) and a drive face (615) of second actuator (614) are each configured to engage with at least a portion of distal coupler (622). In the present example, the same portion of distal coupler (622) engages first actuator (610) and second actuator (614) at different stages of operation. Travel of the at least a portion of distal coupler (622) between first actuator (610) and second actuator (614) is permitted by drive slot (612). It should be understood that this configuration generally results in at least some lost motion between proximal coupler (602) and distal coupler (622) such that in some stages of operation proximal coupler (602) can move without corresponding movement of distal coupler (622).

As described above, first actuator (610) and second actuator (614) together define pivot slot (616). As seen in FIG. 11, pivot slot (616) is positioned on an opposite side of the outer diameter of proximal coupler (602) as drive slot (612). Pivot slot (616) is generally configured to provide space for at least a portion of filter gate (640) to pivot into. In the present example, a portion of second actuator (614) is further shaped to accommodate this pivoting action of filter gate (640). Although second actuator (614) can include a variety of shapes to accommodate this pivoting action, in the present example second actuator (614) generally defines a curved wedge shape.

Figure 13:
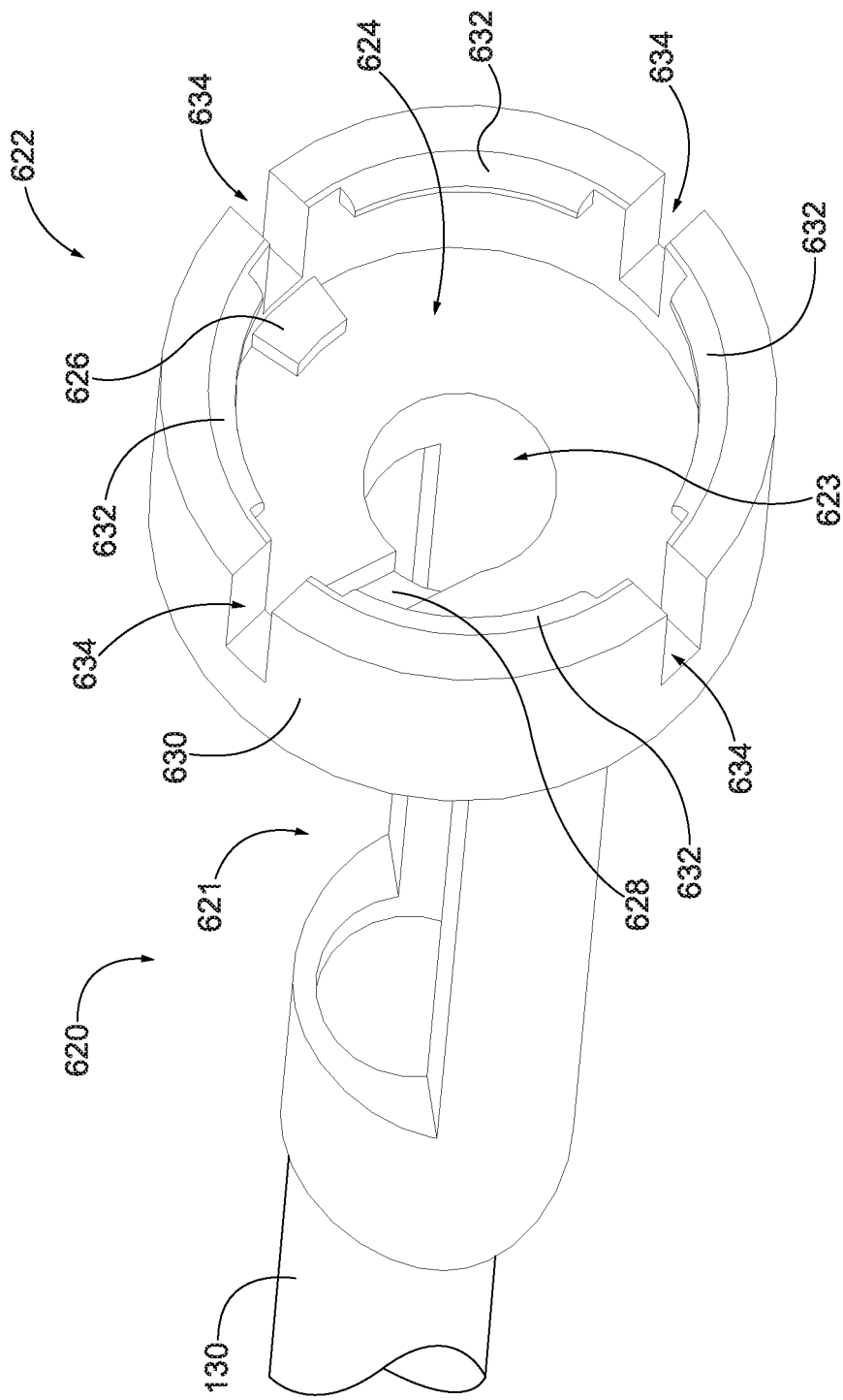
FIG. 13 depicts a perspective view of a distal coupler of the gate assembly of FIG. 5.
Figure 14:
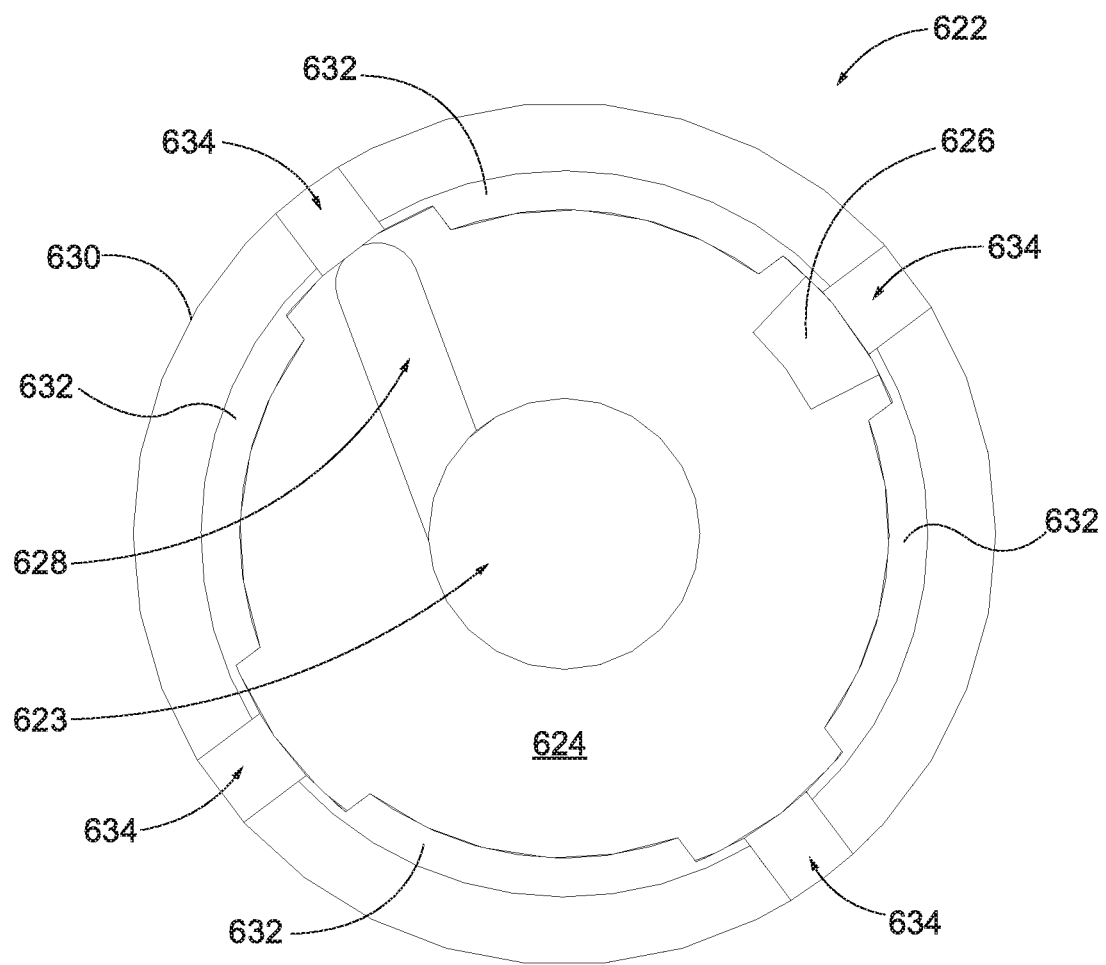
FIG. 14 depicts a rear elevational view of the distal coupler of FIG. 13.

Inspection member (620) and distal coupler (622) are shown in greater detail in FIGS. 13 and 14. As can be seen, inspection member (620) extends distally from distal coupler (622) and is secured to cutter (130). Correspondingly, distal coupler (622) is generally configured to couple to proximal coupler (602). Inspection member (620) defines a sample window (621) that is in communication with a sample lumen (623) extending through inspection member (620) and distal coupler (622). As will be described in greater detail below, the configuration of sample window (621) and sample lumen (623) is generally configured for viewing of a single tissue sample when the single tissue sample is transported through cutter (130), into sample lumen (623), and stopped just distally of distal coupler (622). As will also be described in greater detail below, it should be understood that sample window (621) can also be used to permit external access to sample lumen (623) for removal of the individual tissue sample, thereby permitting physical inspection of the individual tissue sample through palpation or other physical inspection.

Although not shown, it should be understood that in some examples a sensor can be incorporated into sample window (621) to support additional functionalities. For instance, in some examples the sensor can be used to sense certain physical characteristics of the individual tissue sample. In still other examples, the sensor can be used to merely sense to the presence of the individual tissue sample to confirm when the sample is deposited within sample window (621), which can initiate certain changes in vacuum or other fluid control algorithms to facilitate inspection of the individual tissue sample through sample window (621). Of course, various alternative implementations of the sensor can be used as will be apparent to those of ordinary skill in the art in view of the teachings herein.

Distal coupler (622) includes a distal wall (624) and an outer sheath (630) extending proximally from distal wall (624). As will be understood, the combination of distal wall (624) and outer sheath (630) is generally configured to secure distal coupler (622) to proximal coupler (602) to permit controlled transport of tissue samples through gate assembly (600). This controlled transport of tissue samples is generally accomplished through actuation of filter gate (640) via relative movement between proximal coupler (602) and distal coupler (622).

Distal wall (624) includes an actuation protrusion (626) extending proximally from the proximal face of distal wall (624). Actuation protrusion (626) defines a generally trapezoidally-shaped protrusion. As will be described in greater detail below, actuation protrusion (626) is generally configured to engage with at least a portion of proximal coupler (602). In operation, this engagement is used to transfer rotary motion from proximal coupler (602) to distal coupler (622) at various stages of operation. Although actuation protrusion (626) of the present example is shown as having a specific shape, it should be understood that in other examples various alternative shapes can be used. For instance, in some examples actuation protrusion can be triangular, rectangular, square, or rounded. In addition, while actuation protrusion (626) is characterized herein as a protrusion, it should be understood that in other examples actuation protrusion (626) can be configured as an indentation or any other suitable structure that is complementary to other corresponding structures in proximal coupler (602).

Distal wall (624) further defines an actuation channel (628) extending outwardly from sample lumen (623). The outward extension of actuation channel (628) is partially radial in direction. However, the outward extension of actuation channel (628) is not truly radial in the sense that actuation channel (628) projects perpendicularly from the center of distal wall (624). Instead, actuation channel (628) projects at an angle relative to the center of distal wall (624).

In the present example, this angle is approximately tangential relative to sample lumen (623), although other suitable angles can be used. It should be understood that the particular angle of actuation channel (628) is generally configured to drive pivoting of filter gate (640) through a predetermined path. As will be described in greater detail below, actuation channel (628) is configured to receive a portion of filter gate (640) so that the portion of filter gate (640) can translate within actuation channel (628), thereby pivoting filter gate (640) between the sample stopping position and the transport position.

Outer sheath (630) extends proximally from distal wall (624). Outer sheath (630) is generally cylindrical in shape, defining an inner diameter that is approximately equivalent to the outer diameter of proximal coupler (602). As will be understood, outer sheath (630) is generally configured to receive proximal coupler (602) to secure proximal coupler (602) to distal coupler (622). To secure proximal coupler (602) to distal coupler (622), outer sheath (630) includes a plurality of protrusions (632) extending inwardly towards the center of the cylindrical shape defined by outer sheath (630). As will be understood, each protrusion (632) grips a proximal portion of proximal coupler (602) to thereby secure proximal coupler (602) to distal coupler (622). Thus, it should be understood that protrusions (632) generally create a snap-fit assembly between proximal coupler (602) and distal coupler (622).

To promote ease of assembly between proximal coupler (602) and distal coupler (622), outer sheath (630) further includes a plurality of relief channels (634) spaced at equal distances around the perimeter of outer sheath (630). The combination of all relief channels (634) divides outer sheath (630) into a plurality of discrete segments. Because of this, each discrete segment of outer sheath (630) can generally flex outwardly to permit each protrusion to flex into engagement with proximal coupler (602). In the present configuration, outer sheath (630) is divided into four discrete segments with four discrete protrusions (632) corresponding to each segment. In other examples, this configuration can take on a plurality of other forms. For instance, outer sheath (630) can be divided into three or six discrete segments. In addition, or in the alternative, in other examples protrusions (632) are not required to correspond to each discrete segment with a 1:1 ratio as shown. For instance, in some examples each discrete segment can include multiple protrusions (632). Of course, in other examples various alternative configurations can be used as will be apparent to those of ordinary skill in the art in view of the teachings herein.

Figure 16:
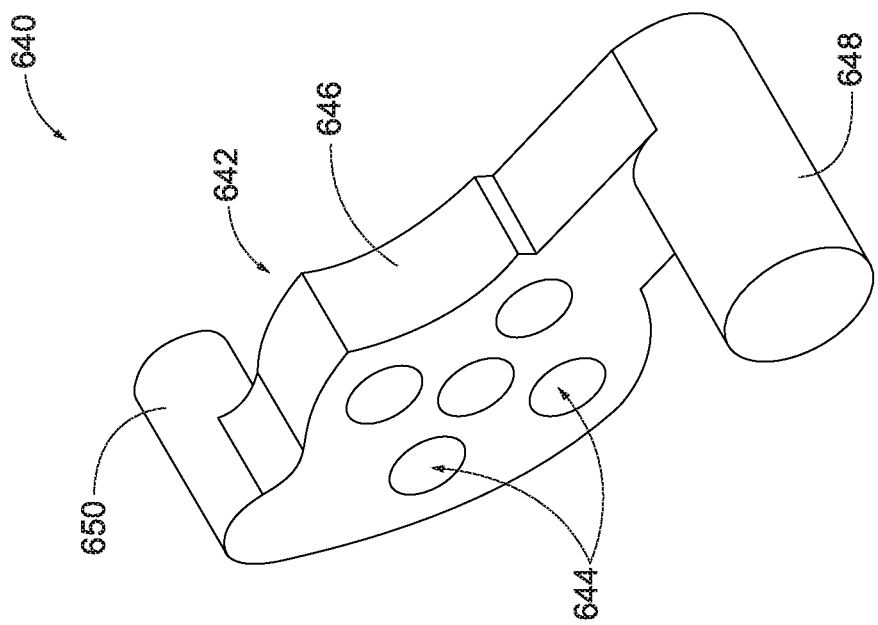
FIG. 16 depicts another perspective view of the filter gate of FIG. 15.
Figure 15:
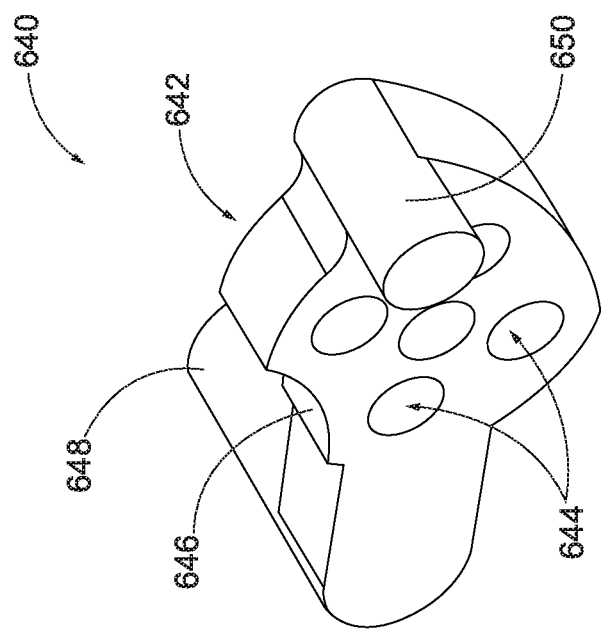
FIG. 15 depicts a perspective view of a filter gate of the gate assembly of FIG. 5.

Filter gate (640) is shown in greater detail in FIGS. 15 and 16. As can be seen, filter gate (640) includes a filter body (642) with a proximal pivot (648) and a distal pivot (650) extending proximally and distally from pivot body (642), respectively. Filter body (642) is generally configured to stop one or more tissue samples distally of filter gate (640) within gate assembly (600) to permit viewing and or inspection of the stopped tissue sample via sample window (621). It should be understood that filter body (642) is further generally configured to permit fluid such as vacuum to flow through filter gate (640) while filter body (642) is stopping one or more tissue samples. To permit the flow of fluid through filter gate (640) via filter body (642), filter body (642) defines a plurality of openings (644) extending between the distal and proximal face of filter body (642). Openings (644) are generally sized to promote the flow of fluids such as vacuum and/or biological or non-biological fluids therethrough, while also preventing the flow of solid tissue samples.

In addition to being configured to stop tissue samples, filter body (642) is also generally configured for manipulation by pivots (648, 650) to permit the flow of samples through gate assembly (600) under certain circumstances. As will be understood, filter body (642) is generally configured to be manipulated into the sample stopping position and the transport position. To support the flow of tissue samples though gate assembly (600) when filter body (642) is in the transport position, filter body (642) includes a cutout (646). Cutout (646) is generally semi-cylindrical in shape with a diameter that generally corresponds transport lumen (619) extending through proximal coupler (602). As will be understood, this shape of cutout (646) is configured to line-up with transport lumen (618) to provide a smooth transition between sample lumen (623) of inspection member (620) and transport lumen (619).

Pivots (648, 650) extend in opposite directions relative to filter body (642). Each pivot (648, 650) is generally configured to engage with a portion of a corresponding coupler (602, 622). For instance, proximal pivot (648) is configured to engage with pivot opening (606) of proximal coupler (602). Similarly, distal pivot is configured to engage with actuation channel (628) of distal coupler (622). To support this engagement, pivots (648, 650) both have a generally cylindrical configuration. As will be described in greater detail below, this configuration generally permits pivots (648, 650) to be manipulated by couplers (602, 622) to thereby manipulate filter body (632) between the sample stopping position and the transport position.

Figure 17:
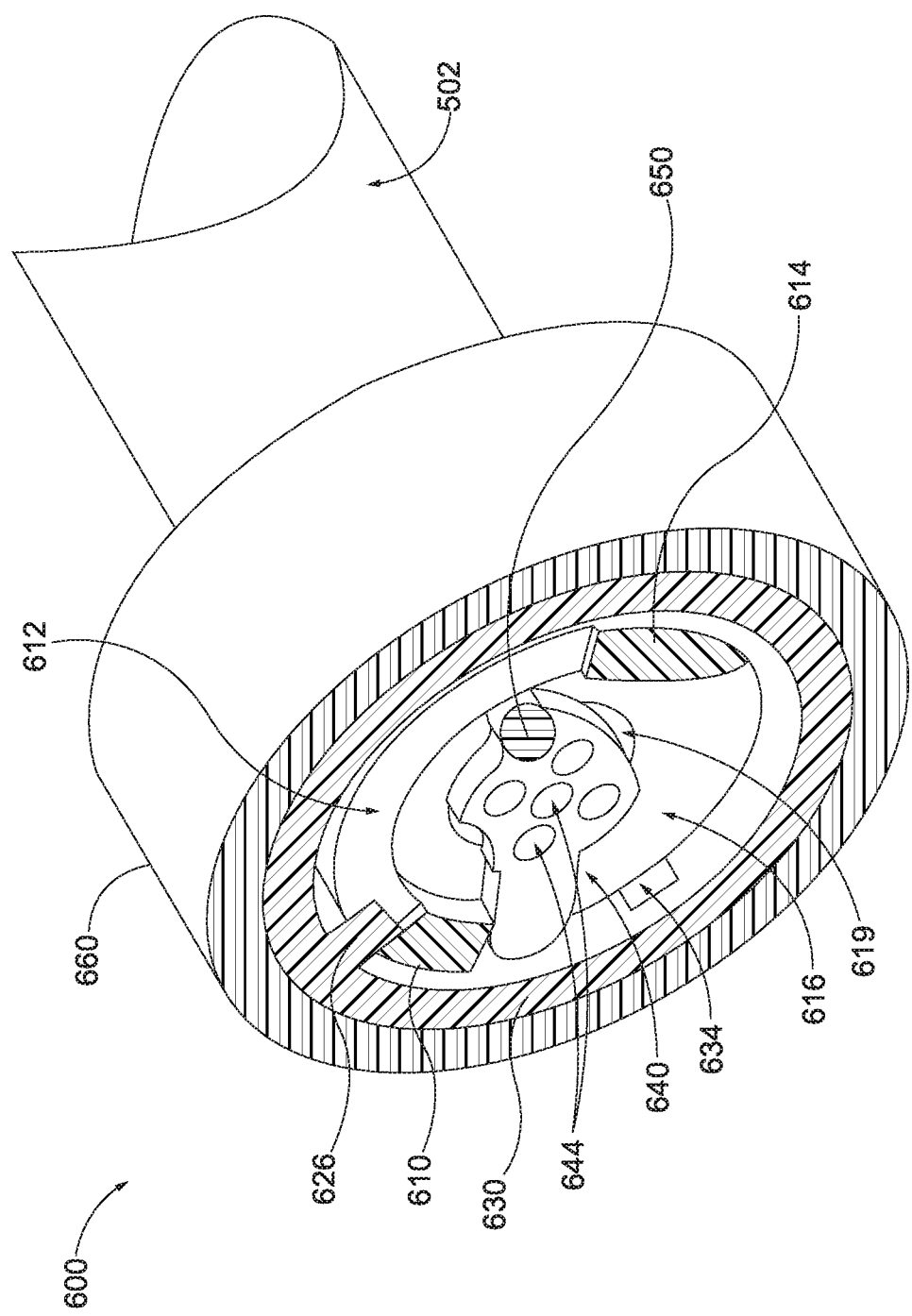
FIG. 17 depicts a perspective cross-sectional view of the gate assembly of FIG. 5, the cross-section taken along line 17-17 of FIG. 9.

As can be seen in FIG. 17, when gate assembly (600) is assembled, filter gate (640) is disposed between proximal coupler (602) and distal coupler (622). It should be understood that when filter gate (640) is in this position, filter gate (640) is generally movable within the cavity formed between proximal coupler (602) and distal coupler (622). As will be described in greater detail below, this configuration permits proximal coupler (602) and distal coupler (622) to manipulate filter gate (640) between the sample stopping position and the transport position.

FIGS. 18A through 20B show an exemplary operation of gate assembly (600). As can be seen, gate assembly (600) initially begins with filter gate (640) in the sample stopping position shown in FIGS. 18A, 19A, and 20A. In the sample stopping position, filter gate (640) is initially positioned to block sample lumen (623) of inspection member (620) and transport lumen (619) of proximal coupler (602). It should be understood that in this position, filter gate (640) generally prevents any tissue sample collected by cutter (130) from being transported through sample lumen (623). Thus, any collected tissue sample is held within inspection member (620) for inspection through sample window (621). Simultaneously, filter gate (640) also permits the flow of vacuum through sample lumen (623) by openings (644) within filter gate (640). This flow of vacuum allows tissue samples to be transported through cutter (130) and sample lumen (623) even when transport lumen (619) is blocked by filter gate (640).

Figure 18A:
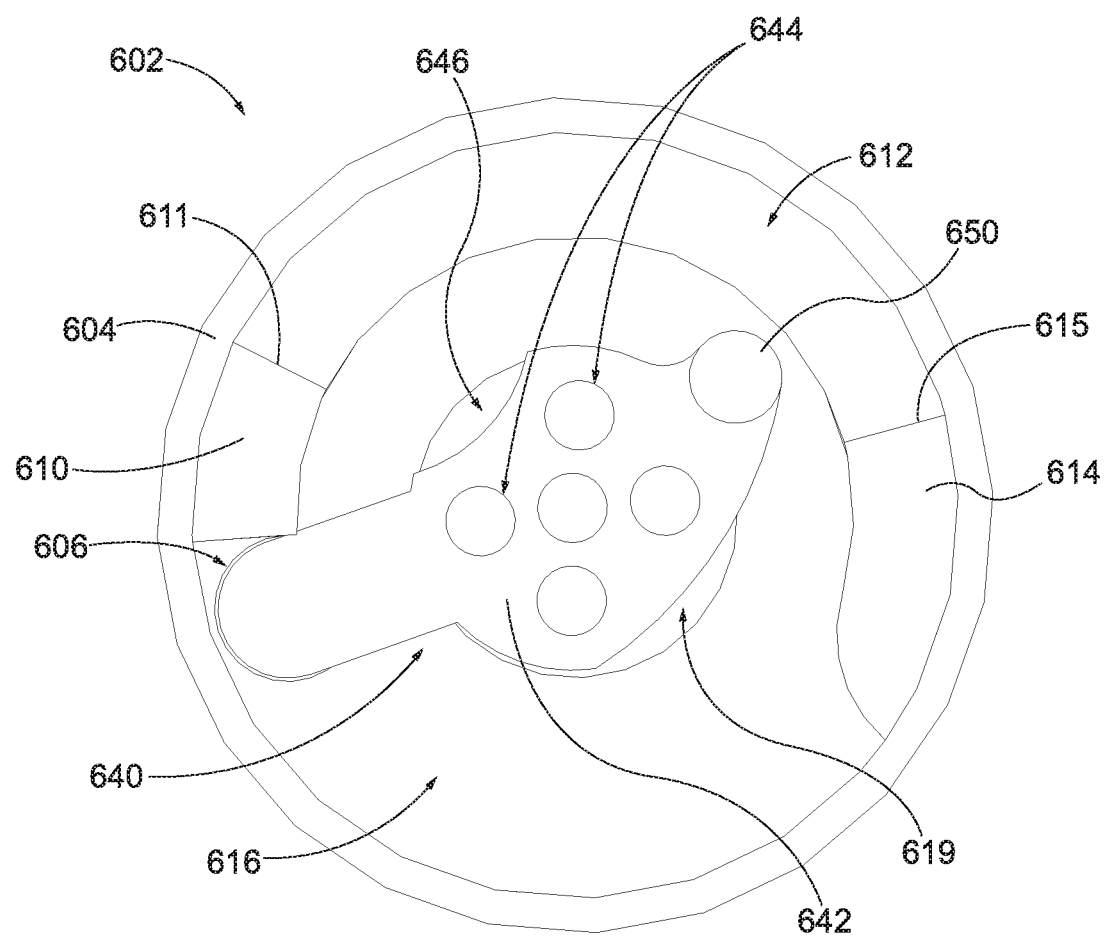
FIG. 18A depicts a front elevational view of the gate assembly of FIG. 5, with the distal coupler of FIG. 13 omitted, the gate assembly in a sample stopping position.
Figure 19A:
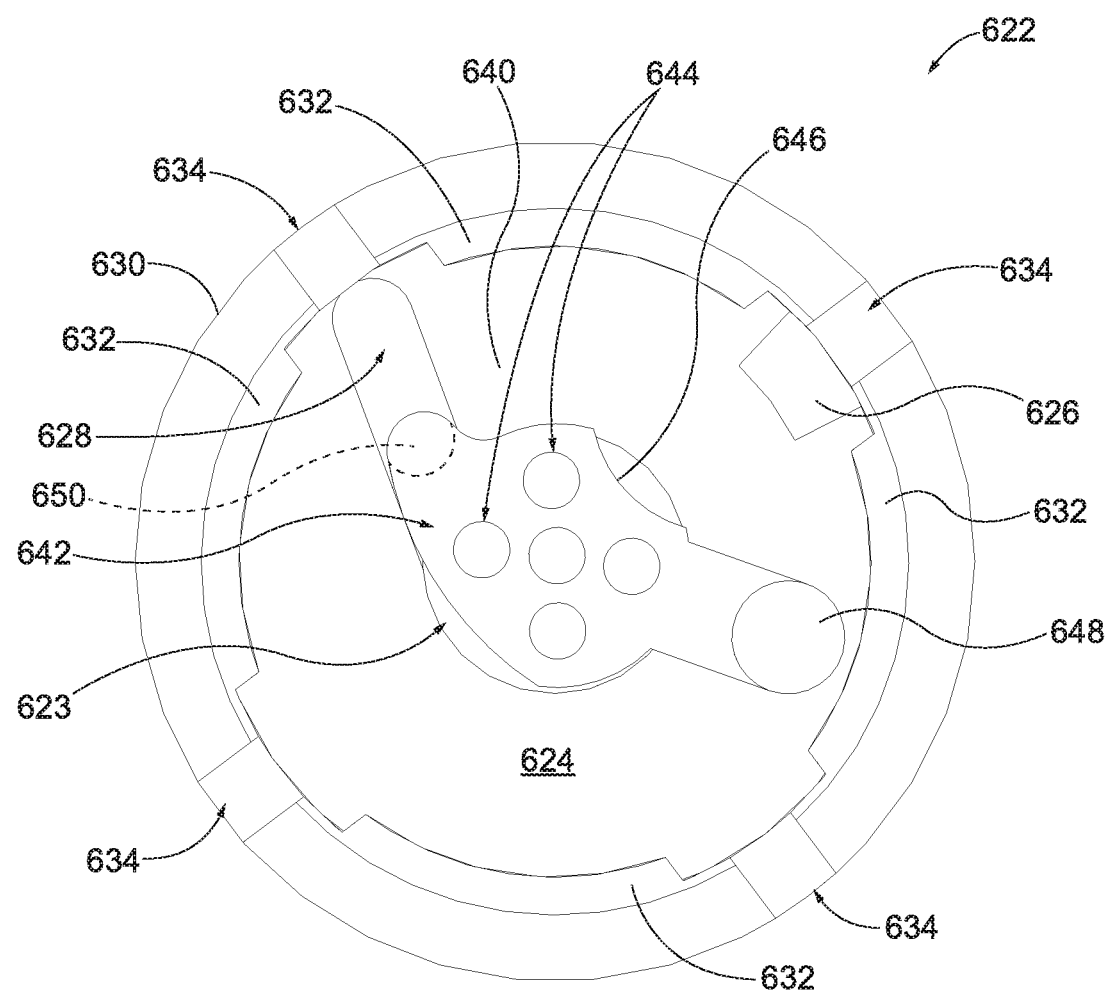
FIG. 19A depicts a rear elevational view of the gate assembly of FIG. 5, with the proximal coupler of FIG. 11 omitted, the gate assembly in the sample stopping position.
Figure 19B:
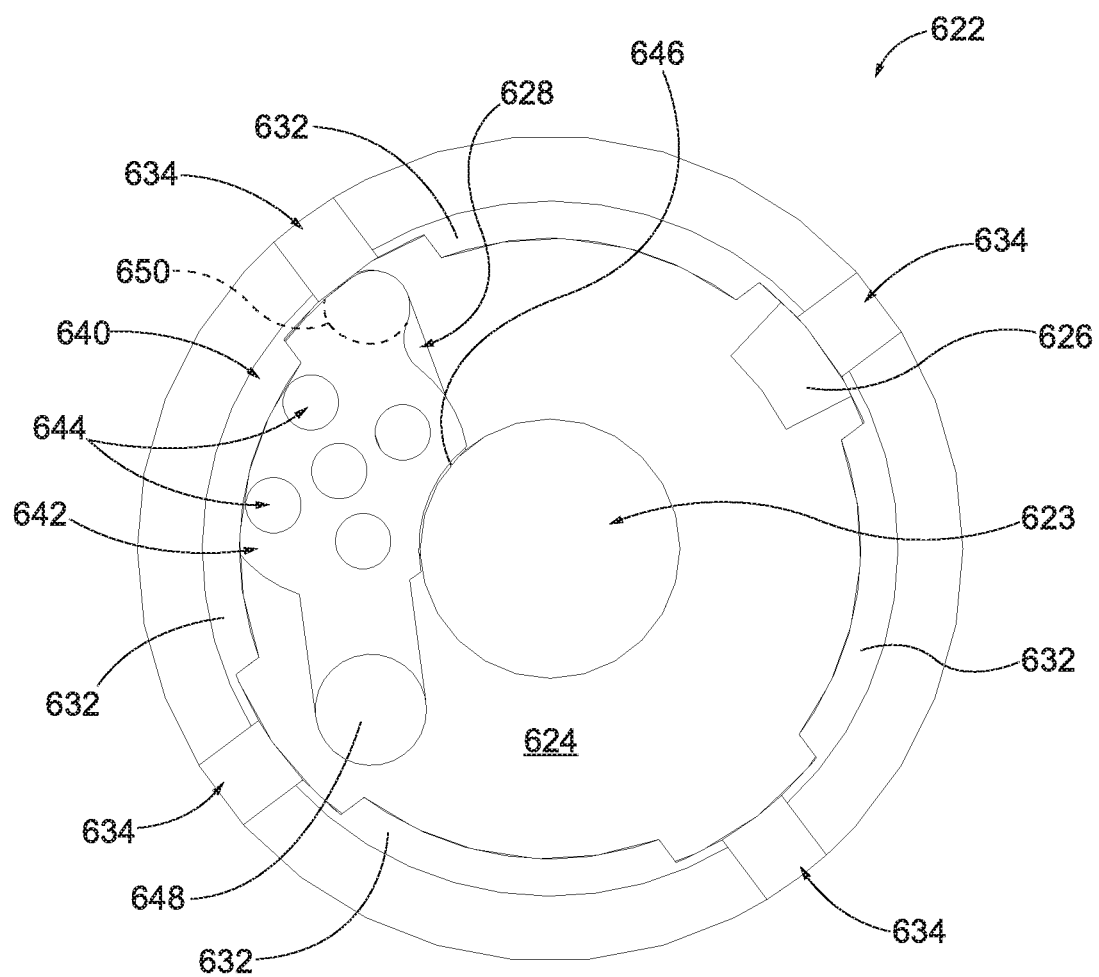
FIG. 19B depicts another rear elevational view of the gate assembly of FIG. 5, with the proximal coupler of FIG. 11 omitted, the gate assembly in the transport position.
Figure 20A:
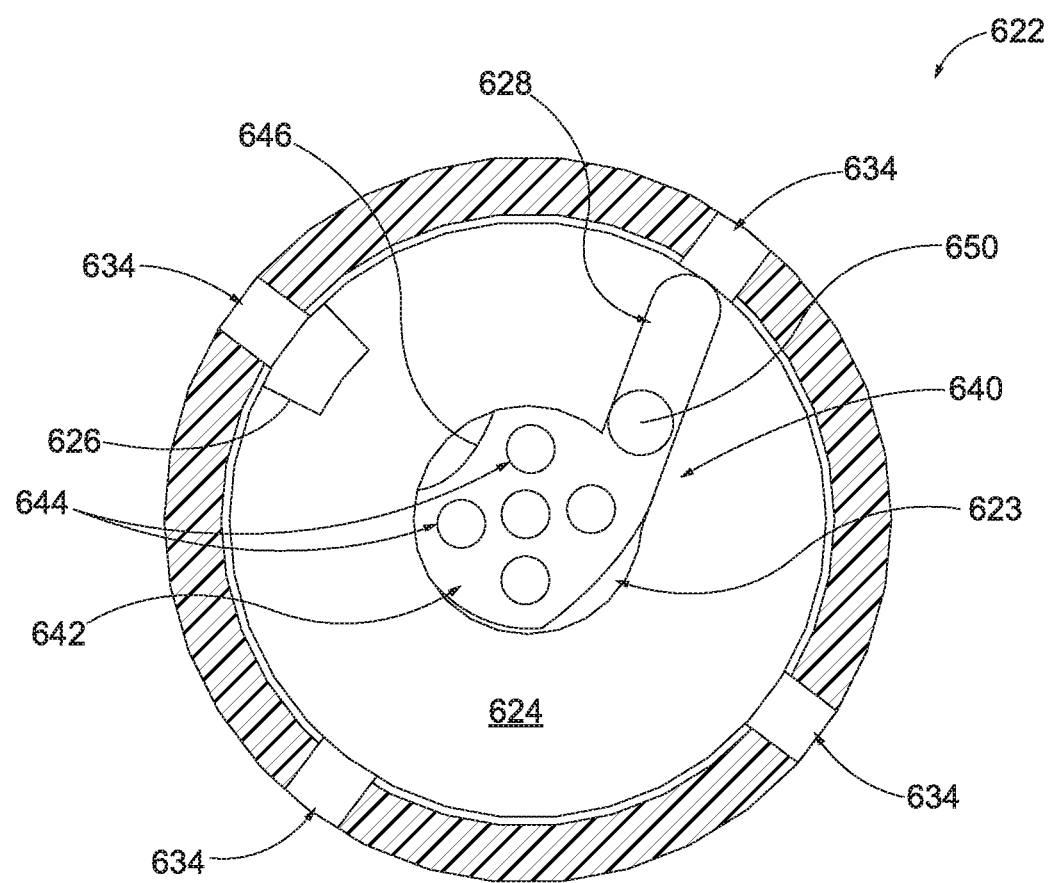
FIG. 20A depicts a front cross-sectional view of the gate assembly of FIG. 5, with the cross-section taken along line 20-20 of FIG. 9, the gate assembly in the sample stopping position.
Figure 20B:
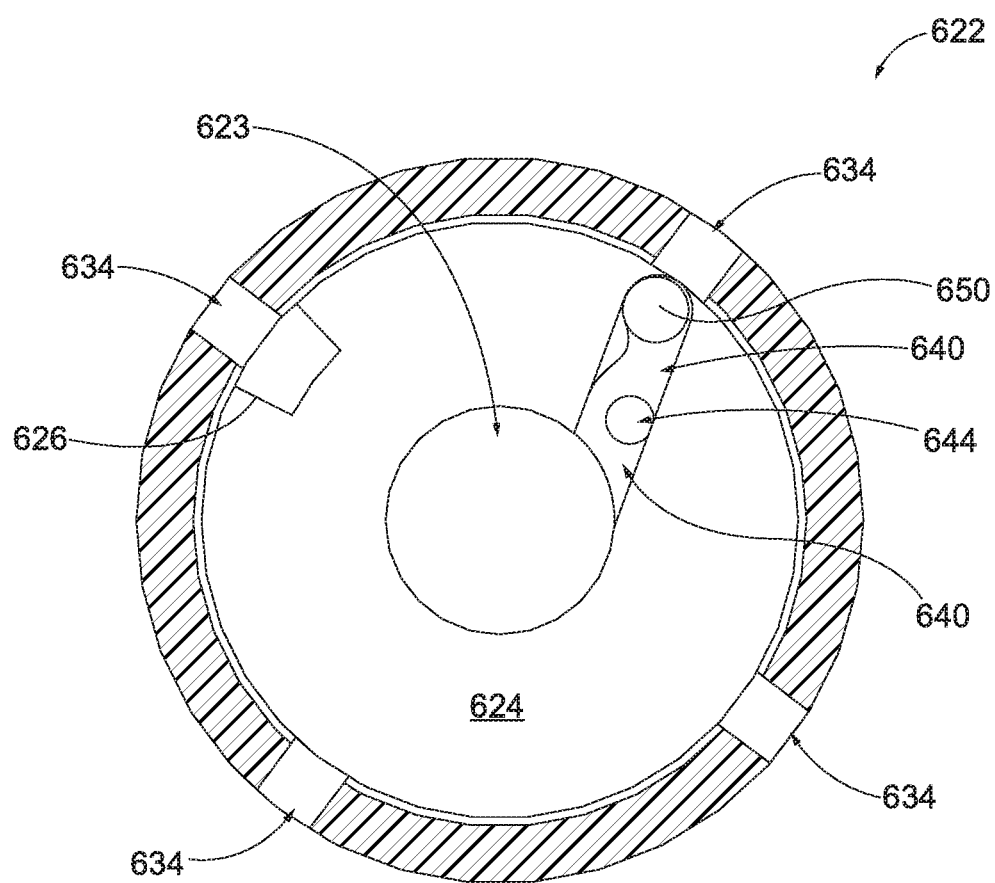
FIG. 20B depicts a front cross-sectional view of the gate assembly of FIG. 5, with the cross-section taken along line 20-20 of FIG. 9, the gate assembly in the transport position.

Filter gate (640) is held in the sample stopping position through engagement between proximal pivot (648) and proximal coupler (602) and distal pivot (650) and distal coupler (622). As best seen in FIG. 18A, proximal pivot (648) is disposed within pivot opening (606) of proximal coupler (602). Meanwhile, as can be seen in FIGS. 19A and 20A, distal pivot (650) is disposed in a lower (or inner) portion of actuation channel (628) of distal coupler (622). Filter gate (640) will remain in the sample stopping position even when proximal coupler (602) and distal coupler (622)

rotate, provided there is little or no relative rotation between proximal coupler (602) and distal coupler (622).

In some uses, this rotation of proximal coupler (602) and distal coupler (622) corresponds to clockwise rotation (e.g., clockwise rotation as shown in FIG. 18A) of proximal coupler (602) and distal coupler (622) that results in distal advancement of cutter (130) to sever a tissue sample. For instance, when proximal coupler (602) is rotated in the clockwise direction in the sample stopping position, first actuator (610) of proximal coupler (602) engages actuation protrusion (626) of distal coupler (622) to cause simultaneous clockwise rotation (e.g., clockwise rotation as shown in FIG. 18A) of distal coupler (622). In use, this rotation can generally correspond to translation of cutter (130) distally to sever a tissue sample.

Figure 18B:
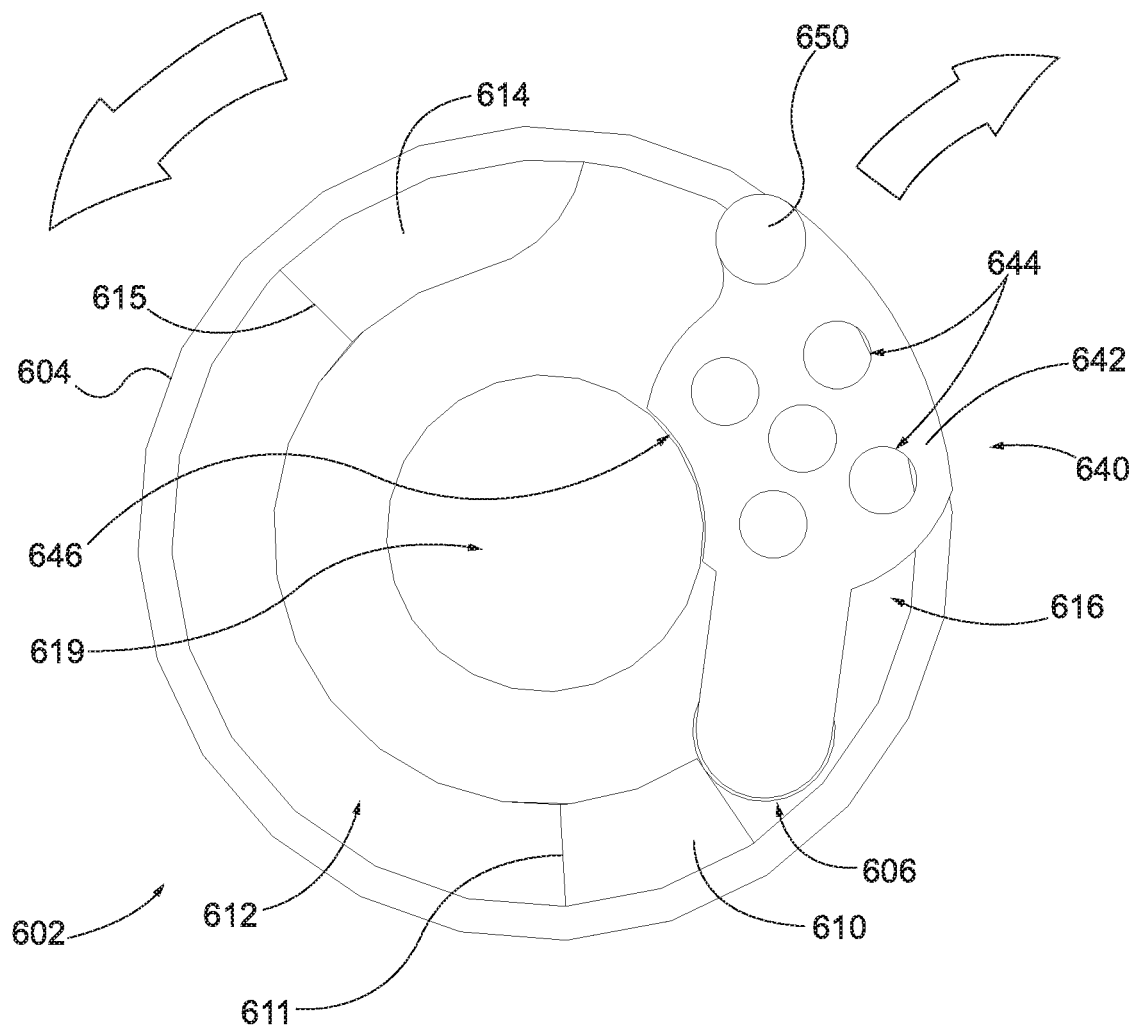
FIG. 18B depicts another front elevational view of the gate assembly of FIG. 5, with the distal coupler of FIG. 13 omitted, the gate assembly in a transport position.

To transition filter gate (640) from the sample stopping position to the transport position, generally at least some relative rotation between proximal coupler (602) and distal coupler (622) occurs. In particular, as can be seen in FIG. 18B, movement of filter gate (640) to the transport position is initiated by proximal coupler (602) rotating in a counter clockwise direction (e.g., counter clockwise direction shown in FIG. 18B). When rotation of proximal coupler (602) begins, it should be understood that distal coupler (622) is generally stationary as actuation protrusion (626) moves within drive slot (612) of proximal coupler (602) between first actuator (610) and second actuator (614). In a biopsy procedure, the moment counter clockwise rotation of proximal coupler (602) generally corresponds to a reversal in translation of cutter (130) from being translated distally to being translated proximally.

When proximal coupler (602) begins to rotate in the counter clockwise direction, proximal pivot (648) of filter gate (640) is moved along with proximal coupler (602) due to engagement between proximal pivot (648) and pivot opening (606) of proximal coupler (602). Proximal pivot (648) moves along a circular path as proximal coupler (602) is rotated. However, it should be understood that as proximal pivot (648) is rotated along the circular path, proximal pivot can also pivot within pivot opening (606) of proximal coupler (602).

As proximal pivot (648) is rotated along the circular path defined by the rotation of proximal coupler (602), distal pivot (650) remains partially fixed. The partial fixation of distal pivot (650) causes the entirety of filter gate (640) to pivot away from transport lumen (619) and into pivot slot (616) of proximal coupler (602). Although distal pivot (650) is partially fixed, it should be understood that at least some movement of distal pivot (650) is permitted. In particular, as described above, distal pivot (650) is received by actuation channel (628) of distal coupler (622). Because actuation channel (628) defines an elongate channel, distal pivot (650) can move along an axis defined by actuation channel (628) within actuation channel (628). This degree of freedom results in distal pivot (650) sliding outwardly relative to the center of distal coupler (622) as filter gate (640) is moved by proximal pivot (648).

As filter gate (640) is pivoted by relative movement between proximal pivot (648) and distal pivot (650), cutout (646) of filter body (642) moves into alignment with sample lumen (623) and transport lumen (619), thereby placing sample lumen (623) in tissue sample communication with transport lumen (619). At this stage (shown in FIGS. 18B, 16B, and 17B), filter gate (640) is in the transport position and a tissue sample can be readily transported from sample lumen (623) and into transport lumen (619).

Once filter gate (640) is in the transport position, further counter clockwise rotation of proximal coupler (602) causes second actuator (614) of proximal coupler (602) to engage actuation protrusion (626) of distal coupler (622) by way of drive face (615). Engagement between drive face (615) of second actuator (614) and actuation protrusion (626) causes proximal coupler (602) and distal coupler (622) to rotate in unison without further movement of filter gate (640). Rotation of both proximal coupler (602) and distal coupler (622) can continue until cutter (130) is fully retracted.

To return filter gate (640) to the sample stopping position, the progression described above is reversed. For instance, proximal coupler (602) will reverse rotation direction back to the clockwise direction. Meanwhile, distal coupler (622) will remain stationary as actuation protrusion (626) is permitted to move within drive slot (612) between second actuator (614) and first actuator (610). This creates relative movement between proximal coupler (602) and distal coupler (622) that drives movement of filter gate (640) back to the sample stopping position in accordance with the description above.

In some examples, gate assembly (600) can be configured to operate in two discrete modes—an automatic mode and a pluck mode. In the automatic mode, filter gate (640) is transitioned between the sample stopping position and the transport position in coordination with translation of cutter (130). For instance, as described above, filter gate (640) is generally in the sample stopping position when cutter (130) is translated distally to sever a tissue sample. Filter gate (640) is then transitioned to the transport position when cutter (130) is translated proximally. This results in an operation that is essentially automatic whereby cutter (130) is advanced to sever a tissue sample, the severed tissue sample is stopped distally of transport lumen (619) for viewing by sample window (621) and then cutter (130) is retracted to permit the severed tissue sample to be transported through transport lumen (619). This process is then repeated for as many samples as is desired.

By contrast, pluck mode decouples the association between translation of cutter (130) and the status of filter gate (640). In some uses, this mode can be desirable to permit an operator to "pluck" a severed tissue sample from sample window (621) for more detailed sample inspection. In the pluck mode, rotation of cutter (130) is decoupled from translation of cutter (130) such that cutter (130) can be translated independently of any rotation. Since the position of filter gate (640) is controlled by what results in rotation of cutter (130), the position of filter gate (640) is not tied to translation of cutter (130) when cutter (130) can be rotated independently of the translation of cutter (130). Although not shown, it should be understood that in examples implementing pluck mode, cutter drive member (502) can be coupled to a cutter drive assembly with separate components for cutter translation and cutter rotation. In some examples, this can include a cutter carriage for translation and an associated elongate spur gear for cutter rotation. Of course, any other suitable cutter drive assembly can be used as will be apparent to those of ordinary skill in the art in view of the teachings herein.

III. BIOPSY DEVICE WITH EXEMPLARY VIEWING TUBE

In some examples it may be desirable to equip biopsy device (10) described above with a viewing tube (680) within sample inspection area (140) of outer housing (210). As will be understood, viewing tube (680) generally acts as a door or selectable barrier for inspection member (620). This functionality can provide generally selectable access to the interior of inspection member (620) to permit a tissue sample to be removed from the interior of inspection member (620) for further inspection. This configuration can be particularly useful in contexts where biopsy device (10) is configured to operate in the pluck mode described above because the independent translation of cutter (130) relative to rotation of cutter (130) can provide this selectability. However, it should be understood that in other examples viewing tube (680) can still be readily used when biopsy device (10) is only configured to operate in the automatic mode described above. Although various structures of viewing tube (680), and viewing tube (680) itself, are described herein as being tubular, it should be understood that in other examples various alternative geometric configurations can be used beyond tubular structures.

Figure 21A:
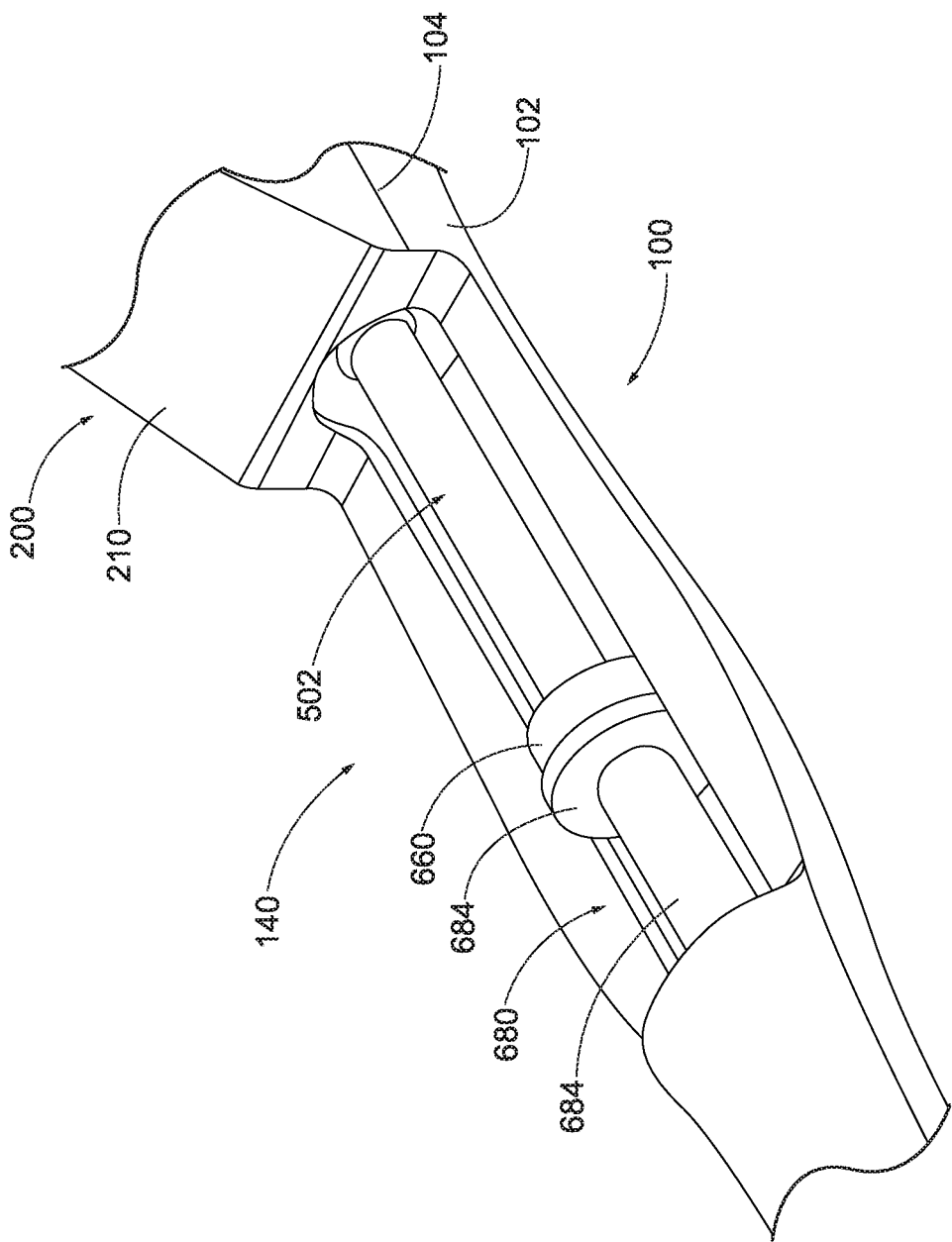
FIG. 21A depicts a detailed perspective view of a sample inspection area of the biopsy device of FIG. 1 equipped with a viewing tube and an inspection member in a distal position.

As best seen in FIG. 21A, viewing tube (680) is generally coaxial with cutter (130) to operatively cover at least a portion of inspection member (620). Viewing tube (680) includes a receiving collar (682) and a cover tube (684). Receiving collar (680) is generally configured to receive at least a portion of coupling collar (660). Thus, receiving collar (680) generally defines an inner diameter that corresponds to the outer diameter of coupling collar (660). In some examples, this inner diameter can be sized to promote an interference fit between coupling collar (660) and receiving collar (680). As will be understood, such an interference fit can promote sealing between coupling collar (660) and receiving collar (680) to prevent fluid leakage from inspection member (620).

Cover tube (684) surrounds sample window (621) of inspection member (620) when inspection member (620) is advanced distally. Although not shown, it should be understood that cover tube (684) can define an internal lumen or chamber to support receiving of inspection member (620). In some examples, the diameter of this internal lumen generally corresponds to the outer diameter of sample window (621) to promote further sealing between viewing tube (680) and inspection member (680).

In the present example, at least cover tube (684) is comprised of a transparent material. This transparent material is generally configured to permit viewing of sample window (621) of inspection member (620) through cover tube (684). To further promote viewing, in some examples receiving collar (680) can also be transparent. Thus, it should be understood that in some examples viewing tube (680) is comprised of an entirely transparent material.

Figure 21B:
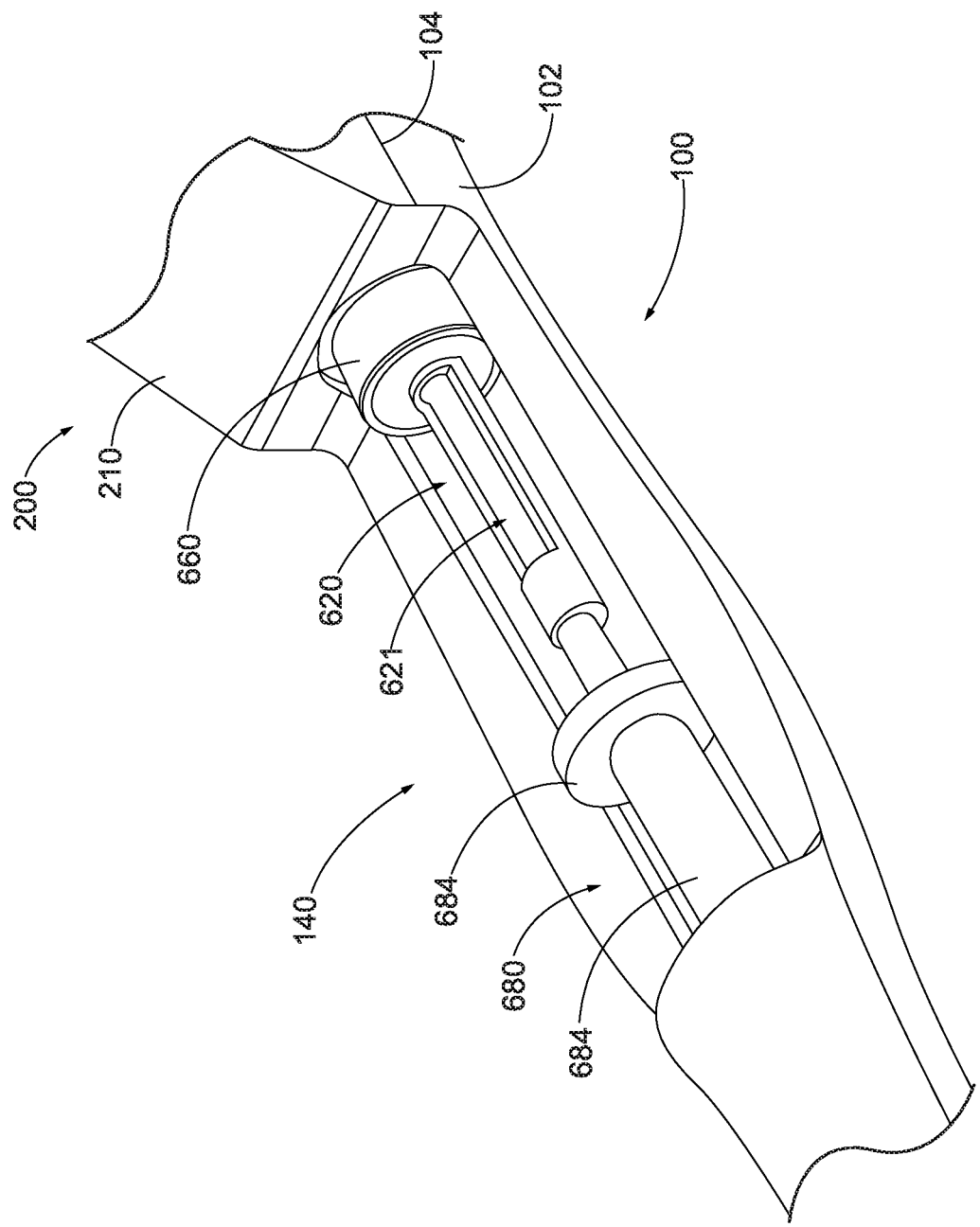
FIG. 21B depicts another detailed perspective view of the sample inspection area of FIG. 21A, the inspection member in a proximal position.

An exemplary use of viewing tube (680) can be shown by comparing FIG. 21A with FIG. 21B. Generally, viewing tube (680) moves through a fixed distal-proximal range of motion along with inspection member (620) during automatic mode. It should be understood that in the automatic mode, the position shown in FIG. 21A corresponds to the proximal-most position of viewing tube (680) and inspection member (620). However, in the pluck mode, inspection member (620) translates through a larger distal-proximal range of motion, while the range of motion of viewing tube (680) is limited to open sample window (621). As will be understood, during the pluck mode, rotation of cutter (130) and inspection member (620) can be limited to prevent centripetal force from ejecting any samples and or fluid while sample window (621) is open.

In the exemplary use described generally above, inspection member (620) can be initially positioned in a viewing position relative to sample inspection area (140) of outer housing (210) as shown in FIG. 21A. In this position, at least a portion of inspection member (620) is positioned within viewing tube (680). In particular, sample window (621) of inspection member (620) is positioned entirely inside of cover tube (684) of viewing tube (680). Meanwhile, coupling collar (660) is received within receiving collar (682) to seal inspection member (620) relative to viewing tube (680).

When inspection member (620) is positioned in the viewing position, cutter (130) can be advanced distally relative to the viewing position to sever a tissue sample. The tissue sample can then be transported through cutter (130) and into inspection member (620). Simultaneously, filter gate (640) is in the sample stopping position to prevent the severed tissue sample from being transported out of inspection member (620). With the severed tissue sample disposed within inspection member (620), the severed tissue sample can be visually inspected through the transparent cover tube (684) by retracting inspection member (620) back to the viewing position shown in FIG. 21A.

If an operator desires to engage in more detailed inspection of the severed tissue sample, inspection member (620) can next be retracted proximally to a pluck position, as shown in FIG. 21B. As described above, cutter actuation assembly (500) can move cutter (130) with independent translation and rotation. Thus, retraction of inspection member (620) from the viewing position to the pluck position can include only translation in some examples to prevent samples or fluid from being ejected from inspection member (620) due to centripetal force.

When inspection member (620) is retracted to the pluck position, viewing tube (680) remains stationary, or has some limited movement such that sample window (621) of inspection member (620) becomes exposed. In some examples, the position of viewing tube (680) can be maintained by one or more protrusions extending from probe body (102). In other words, probe body (102) can include protrusions or other features that act as mechanical stops for viewing tube (680). This permits access to the interior of inspection member (620) so that the severed tissue sample can be removed from inspection member (620) for enhanced inspection techniques (e.g., visual inspection under magnification, palpation, x-ray, and/or etc.).

As described above, the configuration of viewing tube (680) described herein can be particularly beneficial where biopsy device (10) is configured to operate in the pluck mode. When operating in this mode, the severed tissue sample can be placed back into inspection member (620) after being subjected to enhanced inspection techniques. Inspection member (620) can then be translated distally via cutter (130) to the position shown in FIG. 21A. Next, cutter (130) can be rotated independently of any translation to transition filter gate (640) to the transport position to transport the severed tissue sample through transport lumen (619) and into tissue sample holder (300). In some examples, this can be a beneficial operational sequence because transportation of tissue samples can be most effective when inspection member (620) is sealed by viewing tube (680) and vacuum flow is optimal.

In examples where biopsy device (10) is only configured for automatic mode, viewing tube (680) can still be used to provide access to the interior of inspection member (620). However, it should be understood that in such configurations, transportation of severed tissue samples through transport lumen (619) may not be completely optimal due to exposure of sample window (621) of inspection member (620) to atmosphere during transportation. To account for this, in some examples viewing tube (680) can be free to move with inspection member (620) rather than being fixed, or partially fixed, relative to outer housing (210). In this configuration, viewing tube (680) can be manually actuated by an operator to gain access to the interior of inspection member (620) at various stages of operation of biopsy device (10). Thus, this configuration can promote optimal flow of vacuum through inspection member (620) for transport of severed tissue samples, while also providing access to the interior of inspection member (620) for use of enhanced inspection techniques.

Although not shown, it should be understood that in some examples biopsy device (10) can be equipped with one or more sensors to aid in the operation of biopsy device. For instance, in some examples inspection member (620) or viewing tube (680) can be equipped with a sensor configured to detect the presence of a tissue sample received within inspection member (620). Such a sensor can be in communication with a control module or other controller to adjust operational parameters of biopsy device (10) such as vacuum, or cutter movement.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy device comprising: a body; a needle extending distally from the body; a cutter longitudinally translatable relative to the needle, wherein the cutter defines a cutter lumen; a tissue sample holder coupled proximally relative to the body, wherein the cutter lumen of the cutter defines at least a portion of a fluid conduit extending between a distal end of the cutter and the tissue sample holder; and a sample stopping assembly, wherein the sample stopping assembly includes a pivotable strainer that is configured to selectively arrest movement of a tissue sample within the fluid conduit between the cutter and the tissue sample holder.

Example 2

The biopsy device of Example 1, wherein the sample stopping assembly includes a sample inspection member adjacent to the strainer.

Example 3

The biopsy device of Example 2, wherein at least a portion of the sample inspection member is transparent to permit visual inspection of a tissue sample through the sample inspection member.

Example 4

The biopsy device of Examples 2 or 3, wherein the sample inspection member and the strainer are both movable relative to the body to transition the strainer from a sample stopping position to a transport position.

Example 5

The biopsy device of any one or more of Examples 2 through 4, wherein the strainer includes a plurality of vacuum openings, wherein the sample inspection member defines a sample lumen, wherein the strainer is positioned relative to the sample inspection member such that the vacuum openings of the strainer are in fluid communication with the lumen of the sample inspection member.

Example 6

The biopsy device of Example 5, wherein the lumen of the sample inspection member together with the vacuum openings of the strainer are configured to promote the flow of fluid through the strainer when a tissue sample is adjacent to the strainer.

Example 7

The biopsy device of any one or more of Examples 2 through 6, wherein the strainer is rigid.

Example 8

The biopsy device of any one or more of Examples 2 through 7, further including a cutter actuation assembly, wherein the cutter actuation assembly is operable to drive movement of the cutter.

Example 9

The biopsy device of Example 8, wherein the cutter actuation assembly includes a cutter drive member, wherein at least a portion of the cutter drive member is configured to secure the strainer to the sample inspection member of the gate assembly.

Example 10

The biopsy device of Example 9, wherein the sample inspection member includes a lumen, wherein the cutter drive member includes a lumen, wherein the lumens of the sample inspection member and the cutter drive member both define a portion of the fluid conduit extending between the distal end of the cutter and the tissue sample holder.

Example 11

The biopsy device of any one or more of Examples 2 through 10, wherein the strainer is configured to transition between a sample stopping position and transport position, wherein the strainer includes a plurality of openings, wherein each opening of the plurality of openings is configured to permit communication of fluid through the strainer when the strainer is in the sample stopping position.

Example 12

The biopsy device of any one or more of Examples 1 through 11, wherein the sample stopping assembly includes a sensor to detect the presence of a tissue sample within the sample inspection member.

Example 13

The biopsy device of Example 12, wherein the sensor is in communication with a controller, wherein the controller is configured to reduce vacuum supplied to the tissue sample holder in response to detection of the presence of a tissue sample by the sensor.

Example 14

The biopsy device of Example 13, wherein the sensor includes an impedance sensor, wherein the controller is configured to identify characteristics of a tissue sample based on signals from the impedance sensor.

Example 15

The biopsy device of any one or more of Examples 1 through 12, wherein the sample inspection member includes viewing enclosure, wherein at least a portion of the sample stopping assembly is configured to move relative to the viewing enclosure between an open configuration and a closed configuration to permit removal of a tissue sample from the sample stopping assembly.

Example 16

A biopsy device comprising: a body; a needle extending distally from the body; a cutter longitudinally translatable relative to the needle, wherein the cutter defines a cutter lumen; a tissue sample holder coupled proximally relative to the body, wherein the cutter lumen of the cutter defines at least a portion of a fluid conduit extending between the a distal end of the cutter and the tissue sample holder; a cutter actuation assembly, wherein the cutter actuation assembly is configured to translate and rotate the cutter; a sample stopping assembly, wherein the sample stopping assembly an inspection member, and a filter gate, wherein the filter gate is disposed between the inspection member and a portion of the cutter drive assembly, wherein the sample stopping assembly is configured to transition the filter gate between a sample stopping position and a transport position by relative rotation between the inspection member and the cutter drive assembly; and a viewing tube, wherein the viewing tube is configured to receive at least a portion of the inspection member of the tissue stopping assembly, wherein the viewing tube is fixed relative to the body such that the viewing tube is configured to open and close at least a portion of the inspection member of the tissue stopping assembly as the inspection member moves relative to the viewing tube.

Example 17

The biopsy device of Example 16, wherein the cutter drive assembly is configured to rotate and translate the cutter such that rotation and translation of the cutter is independently controllable.

Example 18

The biopsy device of Example 16, wherein the cutter drive assembly is configured to rotate and translate the cutter such that rotation and translation of the cutter is linked thereby resulting in a predetermined relationship between the rotation of the cutter and the translation of the cutter.

Example 19

The biopsy device of Example 18, wherein the cutter drive assembly includes a screw and a nut, wherein rotation of the nut is configured to rotate and translate the cutter.

Example 20

The biopsy device of any one or more of Examples 16 through 19, wherein the viewing tube is transparent to permit viewing of a tissue sample captured within the inspection member through the viewing tube from the exterior of the viewing tube.

Example 21

The biopsy device of any one or more of Examples 16 through 20, wherein the filter gate includes a filter body defining a plurality of openings, a proximal pivot, and a distal pivot.

Example 22

The biopsy device of Example 21, wherein the cutter drive assembly includes a cutter driver, wherein the cutter driver includes a first coupler, wherein the first coupler includes an opening that is configured to receive the proximal pivot of the filter gate.

Example 23

The biopsy device of Example 22, wherein the inspection member includes a second coupler, wherein the second coupler defines a pivot channel, wherein the pivot channel is configured to receive the distal pivot of the filter gate.

Example 24

The biopsy device of Example 23, wherein the first coupler includes a first actuator and a second actuator such that the first actuator and second actuator define a drive slot, wherein the second coupler includes a protrusion, wherein the protrusion of the second coupler is configured to move within the drive slot between the first actuator and second actuator when the filter gate is transitioning between the sample stopping position and the transport position.

Example 25

The biopsy device of Example 16, wherein the filter gate includes a filter body defining a plurality of openings, a proximal pivot, and a distal pivot, wherein the cutter drive assembly includes a cutter driver, wherein the cutter driver includes a first coupler, wherein the first coupler includes an opening that is configured to receive the proximal pivot of the filter gate, wherein the inspection member includes a second coupler, wherein the second coupler defines a pivot channel, wherein the pivot channel is configured to receive the distal pivot of the filter gate, wherein the first coupler includes a first actuator and a second actuator such that the first actuator and second actuator define a drive slot, wherein the second coupler includes a protrusion, wherein the protrusion of the second coupler is configured to move within the drive slot between the first actuator and second actuator when the filter gate is transitioning between the sample stopping position and the transport position.

Example 26

A biopsy device comprising: a holster; a probe including a needle extending distally from the probe and a cutter longitudinally translatable relative to a tissue receiving aperture defined by the needle, wherein the cutter defines a cutter lumen; a transfer tube at least partially defining a conduit extending between a distal end of the cutter and a tissue sample holder; and a sample stopping assembly, wherein the sample stopping assembly includes a first coupler, a second coupler, and a filter gate disposed between the first coupler and the second coupler, wherein the sample stopping assembly is configured to transition the filter gate between a sample stopping position and a transport position by relative motion between the first coupler and the second coupler.

Example 27

The biopsy device of Example 26, wherein the sample stopping assembly includes a sample inspection member.

Example 28

The biopsy device of Example 27, wherein the sample inspection member including a sensor to detect the presence of a tissue sample within the sample inspection member.

Example 29

The biopsy device of Example 28, wherein the sensor is in communication with a controller, wherein the controller is configured to reduce vacuum supplied to the tissue sample holder in response to detection of the presence of a tissue sample by the sensor.

Example 30

The biopsy device of any one or more of Examples 27 through 29, further comprising an access window, wherein the sample inspection member is configured to move relative to the access window between an open configuration and a closed configuration to permit removal of a tissue sample from the sample inspection member.

Example 31

The biopsy device of any one or more of Examples 26 through 30, wherein the filter gate of the sample stopping assembly includes a plurality of openings, wherein the openings are configured to communicate fluid through the filter gate when the filter gate is in the sample stopping position.

Example 32

The biopsy device of any one or more of Examples 26 through 31, wherein the first coupler and a second coupler each define a lumen, wherein the filter gate is configured to substantially block the lumen of the first coupler and the second coupler when the filter gate is in the sample stopping position, wherein the filter gate is configured to not block the lumen of the first coupler and the second coupler when the filter gate is in the transport position.

Example 33

The biopsy device of Example 32, wherein the conduit at least partially defined by the transport tube is further at least partially defined by the lumen of the first coupler and the lumen of the second coupler.

Example 34

The biopsy device any one or more of Examples 26 through 33, wherein the cutter is configured to translate between a proximal position and a distal position, wherein the filter gate is configured to translate with the cutter as the cutter translates between the proximal position and the distal position.

Example 35

The biopsy device of Example 34, wherein the filter gate is configured to be in the transport position when the cutter is in the proximal position, wherein the filter gate is configured to be in the transport position when the cutter is on the distal position.

Example 36

A method for collecting tissue samples using a biopsy device, the method comprising: transporting a first tissue sample through a cutter of the biopsy device to a sample viewing portion of the biopsy device; arresting the first tissue sample in the sample viewing portion; inspecting the first tissue sample while the first tissue sample is disposed within the viewing portion; transporting the first tissue sample from the sample viewing portion to a tissue sample holder, wherein the step of transporting includes pivoting a filter gate from a sample stopping position to a transport position; and transporting a second tissue sample through the cutter to the sample viewing portion.

Example 37

The method of Example 36, wherein the step of inspecting the first tissue sample includes visual inspection of the first tissue sample.

Example 38

The method of any one or more of Examples 36 through 37, further comprising removing the first tissue sample from the sample viewing portion to inspect the first tissue sample by palpitation.

Example 39

The method of any one or more of Examples 36 through 38, wherein the step of inspecting the first tissue sample includes translating the cutter without rotating the cutter to open at least a portion of an inspection member.

Example 40

The method of any one or more of Examples 36 through 38, wherein the step of transporting the first tissue sample from the sample viewing portion to the sample holder includes pivoting the filter gate by rotation of the cutter, wherein the rotation of the cutter is performed while translating the cutter.

V. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A biopsy device comprising:
   (a) a body;
   (b) a needle extending distally from the body;
   (c) a cutter longitudinally translatable relative to the needle, wherein the cutter defining a cutter lumen;
   (d) a cutter drive assembly, the cutter drive assembly being configured to selectively drive rotation and translation of the cutter;
   (e) a tissue sample holder coupled proximally relative to the body, wherein the cutter lumen of the cutter defining at least a portion of a fluid conduit extending between a distal end of the cutter and the tissue sample holder; and
   (f) a sample stopping assembly, the sample stopping assembly including a rotatable strainer that is configured to selectively arrest movement of a tissue sample within the fluid conduit between the cutter and the tissue sample holder, the rotatable strainer being further configured to move in response to lost motion between a distal coupler associated with the cutter and a proximal coupler associated with the cutter drive assembly.

2. The biopsy device of claim 1, the sample stopping assembly including a sample inspection member adjacent to the strainer.

3. The biopsy device of claim 2, at least a portion of the sample inspection member being transparent to permit visual inspection of a tissue sample through the sample inspection member.

4. The biopsy device of claim 2, the strainer being movable relative to the body and the sample inspection member to transition the strainer from a sample stopping position to a transport position.

5. The biopsy device of claim 2, the strainer including a plurality of vacuum openings, the sample inspection member defining a sample lumen, the strainer being positioned relative to the sample inspection member such that the vacuum openings of the strainer are in fluid communication with the lumen of the sample inspection member.

6. The biopsy device of claim 5, the lumen of the sample inspection member together with the vacuum openings of the strainer being configured to promote the flow of fluid through the strainer when a tissue sample is adjacent to the strainer.

7. The biopsy device of claim 2, the strainer being rigid.

8. The biopsy device of claim 2, the cutter actuation assembly including a cutter drive member, at least a portion of the cutter drive member being configured to secure the strainer to the sample inspection member of the sample stopping assembly.

9. The biopsy device of claim 8, the sample inspection member including a lumen, the cutter drive member including a lumen, the lumen of the sample inspection member and the lumen of the cutter drive member both defining a portion of the fluid conduit extending between the distal end of the cutter and the tissue sample holder.

10. The biopsy device of claim 2, the strainer being configured to transition between a sample stopping position and a transport position, the strainer including a plurality of openings, each opening of the plurality of openings being configured to permit communication of fluid through the strainer when the strainer is in the sample stopping position.

11. The biopsy device of claim 1, the sample stopping assembly including a sensor to detect the presence of a tissue sample within the sample inspection member.

12. The biopsy device of claim 11, further comprising a controller, the sensor being in communication with the controller, the controller being configured to reduce vacuum supplied to the tissue sample holder in response to detection of the presence of a tissue sample by the sensor.

13. The biopsy device of claim 12, the sensor including an impedance sensor, the controller being configured to identify characteristics of a tissue sample based on signals from the impedance sensor.

14. The biopsy device of claim 2, the sample inspection member including viewing enclosure, at least a portion of the sample stopping assembly being configured to move relative to the viewing enclosure between an open configuration and a closed configuration to permit removal of a tissue sample from the sample stopping assembly.

15. A biopsy device comprising:
   (a) a body;
   (b) a needle extending distally from the body;
   (c) a cutter longitudinally translatable relative to the needle, the cutter defining a cutter lumen;
   (d) a tissue sample holder coupled proximally relative to the body, the cutter lumen of the cutter defining at least a portion of a fluid conduit extending between a distal end of the cutter and the tissue sample holder;
   (e) a cutter actuation assembly, the cutter actuation assembly being configured to translate and rotate the cutter;
   (f) a sample stopping assembly, the sample stopping assembly including an inspection member, and a filter gate, the filter gate being disposed between the inspection member and a portion of the cutter drive assembly, the sample stopping assembly being configured to transition the filter gate between a sample stopping position and a transport position by relative rotation between the inspection member and the cutter drive assembly and
   (g) a viewing tube, the viewing tube being configured to receive at least a portion of the inspection member of the tissue stopping assembly, the viewing tube being fixed relative to the body such that the viewing tube is configured to open and close at least a portion of the inspection member of the tissue stopping assembly as the inspection member moves relative to the viewing tube.

16. The biopsy device of claim 15, the cutter drive assembly being configured to rotate and translate the cutter such that rotation and translation of the cutter is independently controllable.

17. The biopsy device of claim 15, the cutter drive assembly being configured to rotate and translate the cutter such that rotation and translation of the cutter is linked thereby resulting in a predetermined relationship between the rotation of the cutter and the translation of the cutter.

18. The biopsy device of claim 17, the cutter drive assembly including a translation member and a rotation member, rotation of the translation member and rotation member being configured to rotate and translate the cutter.

19. A biopsy device comprising:
   (a) a holster;
   (b) a probe including a needle extending distally from the probe and a cutter longitudinally translatable relative to a tissue receiving aperture defined by the needle, the cutter defining a cutter lumen;
   (c) a transfer tube at least partially defining a conduit extending between a distal end of the cutter and a tissue sample holder; and
   (d) a sample stopping assembly, the sample stopping assembly including a first coupler, a second coupler, and a filter gate disposed between the first coupler and the second coupler, the first coupler and the second coupler being configured to move separately relative to each other, the sample stopping assembly being configured to transition the filter gate between a sample stopping position and a transport position by relative motion between the first coupler and the second coupler.

* * * * *